(12) United States Patent
Troy et al.

(10) Patent No.: US 9,266,625 B1
(45) Date of Patent: Feb. 23, 2016

(54) SYSTEM AND METHOD FOR SCANNING A WING BOX SKIN

(71) Applicant: The Boeing Company, Chicago, IL (US)

(72) Inventors: James J. Troy, Issaquah, WA (US); William P. Motzer, Seattle, WA (US); Scott W. Lea, Renton, WA (US); James C. Kennedy, Renton, WA (US); Michael C. Hutchinson, Kent, WA (US)

(73) Assignee: The Boeing Company, Chicago, IL (US)

( * ) Notice: Subject to any disclaimer, the term of this patent is extended or adjusted under 35 U.S.C. 154(b) by 520 days.

(21) Appl. No.: 13/859,278

(22) Filed: Apr. 9, 2013

Related U.S. Application Data

(63) Continuation-in-part of application No. 13/534,014, filed on Jun. 27, 2012, now Pat. No. 9,010,684.

(51) Int. Cl.
*G05D 7/00* (2006.01)
*G06F 1/26* (2006.01)
*G01N 29/04* (2006.01)
*B64F 5/00* (2006.01)
*G01N 29/26* (2006.01)
*G01N 29/265* (2006.01)

(52) U.S. Cl.
CPC ............. *B64F 5/0045* (2013.01); *G01N 29/26* (2013.01); *G01N 29/265* (2013.01); *G01N 2291/26* (2013.01); *G01N 2291/2694* (2013.01)

(58) Field of Classification Search
CPC .. B64F 5/0045; G01N 29/043; G01N 29/225; G01N 29/265; G01N 2291/0231; G01N 2291/2694
See application file for complete search history.

(56) References Cited

U.S. PATENT DOCUMENTS

| | | | | |
|---|---|---|---|---|
| 4,138,822 A | * | 2/1979 | Parodi | B23Q 1/015 33/572 |
| 4,741,015 A | * | 4/1988 | Charrier | A61B 6/4441 378/196 |
| 5,713,250 A | * | 2/1998 | Hendricks | B25B 23/14 173/2 |
| 6,722,202 B1 | | 4/2004 | Kennedy et al. | |
| 6,881,925 B1 | * | 4/2005 | Sato | B23K 26/106 219/121.73 |
| 6,993,971 B2 | | 2/2006 | Bossi et al. | |
| 7,231,826 B2 | | 6/2007 | Bossi et al. | |
| 7,249,512 B2 | | 7/2007 | Kennedy et al. | |

(Continued)

OTHER PUBLICATIONS

U.S. Appl. No. 12/966,268, filed Dec. 13, 2010, entitled "Device and Method for Inspecting a Corner Radius."

(Continued)

*Primary Examiner* — Ramesh Patel
(74) *Attorney, Agent, or Firm* — Ostrager Chong Flaherty & Broitman P.C.

(57) ABSTRACT

Systems and methods for automated non-destructive inspection scanning of the top and bottom aerodynamic surfaces or skins of an integrally stiffened wing box (e.g., a horizontal stabilizer) using surface crawling vehicles. Each system uses dynamically controlled magnetic coupling to couple an external drive tractor to a pair of passive trailers disposed in the interior of the wing box on opposite sides of a spar. The external drive tractor is also coupled to an external NDI scanner, which the tractor pushes or pulls across the surface skin being inspected. The systems allow scanning of both surface skins without turning the wing box over. Each system is modular and can be transported to and easily set up in a building or factory.

24 Claims, 15 Drawing Sheets

(56) References Cited

U.S. PATENT DOCUMENTS

| | | | |
|---|---|---|---|
| 7,263,889 B2 | 9/2007 | Kennedy et al. | |
| 7,484,413 B2 * | 2/2009 | Georgeson | G01N 29/07 73/624 |
| 7,669,799 B2 * | 3/2010 | Elzey | B32B 3/28 244/123.1 |
| 7,789,339 B2 * | 9/2010 | Sommer | B64C 37/02 244/117 R |
| 2002/0017140 A1 * | 2/2002 | Georgeson | G01N 29/225 73/618 |
| 2007/0006657 A1 | 1/2007 | Kennedy et al. | |
| 2008/0256788 A1 * | 10/2008 | Glazebrook | B23P 19/10 29/700 |
| 2010/0095775 A1 | 4/2010 | Sarr et al. | |
| 2010/0100085 A1 * | 4/2010 | Lewinsky | A61B 18/22 606/16 |
| 2010/0116938 A1 * | 5/2010 | Kline | B29C 65/5042 244/131 |
| 2010/0157276 A1 * | 6/2010 | Shibazaki | G03F 7/70341 355/72 |
| 2010/0296070 A1 * | 11/2010 | Shibazaki | G03F 7/70733 355/53 |
| 2012/0043422 A1 * | 2/2012 | Campana | B64C 1/26 244/123.1 |
| 2013/0081830 A1 * | 4/2013 | Tuttle | A01B 63/22 172/1 |

OTHER PUBLICATIONS

U.S. Appl. No. 13/313,267, filed Dec. 7, 2011, entitled "Adaptive Magnetic Coupling System."

Troedsson, "Automated ultrasonic field inspection on aircrafts with CFRP composite structure," ATX 2006—Aero NDT Forum, Hamburg, Apr. 5, 2006.

Skramstad, "Improved Methods for Ultrasonic Inspection of Large Carbon Fiber Composite Wing Structure," ATA NDT Forum, Sep. 27, 2011.

* cited by examiner

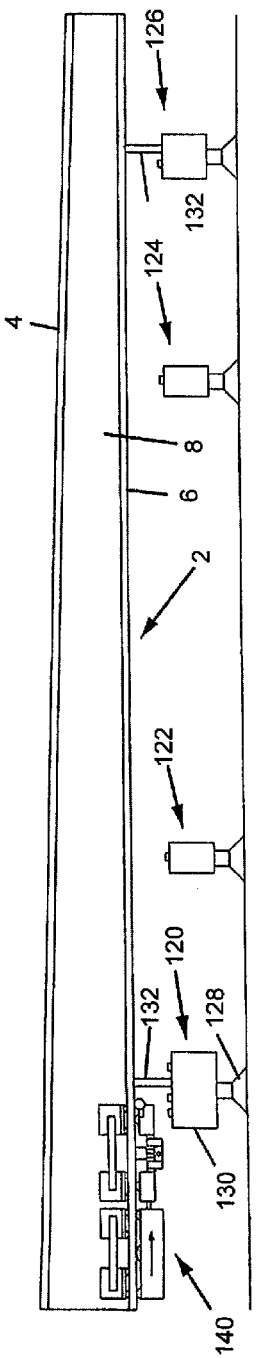
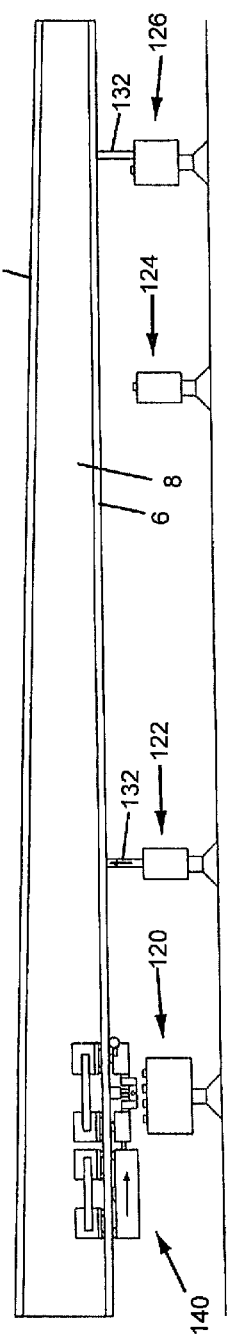
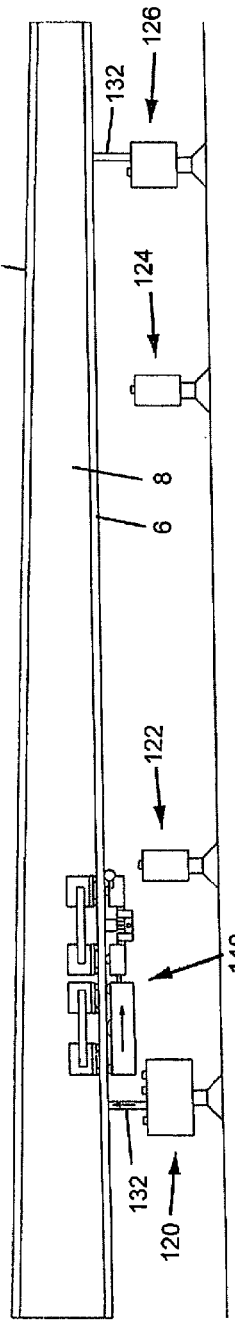

SYSTEM AND METHOD FOR SCANNING A WING BOX SKIN

RELATED PATENT APPLICATION

This application is a continuation-in-part of and claims priority from U.S. patent application Ser. No. 13/534,014 filed on Jun. 27, 2012.

BACKGROUND

The present disclosure relates generally to the field of automated maintenance (including non-destructive inspection) of aircraft structural elements, and more particularly to an automated end effector-carrying apparatus that is coupled to and travels along an integrally stiffened wing box while performing a maintenance function. As used herein, the term "maintenance" includes, but is not limited to, operations such as non-destructive inspection (NDI), visual inspection, drilling, scarfing, grinding (e.g., to remove bonded or bolted components), fastening, appliqué application, ply mapping, depainting, cleaning and painting.

A variety of elongated composite structures may have relatively confined internal cavities that require inspection in order to assure that the structure meets production and/or performance specifications. One known elongated composite structure with tapering internal cavities is an integrally stiffened wing box for an airplane. One example application is in the horizontal stabilizer of an aircraft. A horizontal stabilizer structural box may be fabricated as a large co-cured structure that requires the use of soft internal tools to facilitate tool removal after the cure. If a given co-cured composite structure is considered primary structure, it would therefore need to be inspected to ensure structural integrity.

One of the requirements for certification of a composite-based airplane horizontal stabilizer is to perform a complete set of NDI scan of all the composite structural elements. Methods for scanning the interior surfaces of a horizontal stabilizer using a modular, magnetically coupled transporter system have been disclosed, for example, in U.S. patent application Ser. No. 13/534,014. With regard to the exterior surfaces of a horizontal stabilizer, it is known to use a large gantry mechanism that moves an ultrasonic maintenance tool over a surface skin. This gantry-based system is expensive, requires extensive training to operate, and occupies a large space, which limits the flexibility in setting up NDI work cells for scanning of horizontal stabilizers It also requires that the horizontal stabilizer be turned over to scan the opposite surface.

It would be desirable if a process were available that could scan wing box surface skins without the need for a gantry-based mechanism for movement of the NDI sensor array. An additional benefit would be if the surface skin scanning process were compatible with the aforementioned process for scanning the interior surfaces. Accordingly, there is a need for a system for inspecting the exterior of a wing box and similar elongated hollow structures that can provide such benefits.

SUMMARY

The subject matter disclosed herein includes systems and methods for automated NDI scanning of the top and bottom aerodynamic surfaces or skins of an integrally stiffened wing box (e.g., a horizontal stabilizer) using surface crawling vehicles. In accordance with various embodiments disclosed herein, the system uses dynamically controlled magnetic coupling to couple an external drive tractor to a pair of passive trailers disposed inside a wing box on opposite sides of a spar. The externally mounted drive tractor is also coupled to an externally mounted payload platform, which the tractor pushes or pulls across the surface skin being inspected. The disclosed systems allow scanning of both surface skins without turning the integrally stiffened wing box over. Each system is modular and can be transported to and easily set up in a building or factory.

One aspect of the subject matter disclosed herein is a method for scanning a wing box skin, comprising: (a) placing a first tractor vehicle in a position external to the wing box and in contact with the skin; (b) placing first and second trailer vehicles in respective interior spaces of the wing box with a first spar of the wing box therebetween; (c) magnetically coupling the first and second trailer vehicles to the first tractor vehicle with the skin therebetween and to each other with the first spar therebetween; (d) coupling a payload platform to the first tractor vehicle in a position external to the wing box, the payload platform comprising a frame and a maintenance tool that is movable relative to the frame; (e) moving the first tractor vehicle along a path that follows the first spar; (f) stopping the first tractor vehicle; and (g) moving the maintenance tool of the payload platform in a first direction relative to the frame of the payload platform while the first tractor vehicle is stopped in step (f). The foregoing method may further comprise: (h) placing a second tractor vehicle in a position external to the wing box and in contact with the skin; (i) placing third and fourth trailer vehicles in respective interior spaces of the wing box with a second spar of the wing box therebetween; (j) magnetically coupling the third and fourth trailer vehicles to the second tractor vehicle with the skin therebetween and to each other with the second spar therebetween; (k) coupling the payload platform to the second tractor vehicle; (l) during step (e), moving the second tractor vehicle along a path that follows the second spar; and (m) stopping the second tractor vehicle, wherein step (g) is performed while the first and second tractor vehicles are not moving. The maintenance tool can be an inspection unit that transmits beams toward the skin and receives reflection signals returned to the inspection unit receiver.

In accordance with another aspect, the scanning method set forth in the preceding paragraph may further comprise the following steps: placing first, second and third wing box support tools under the wing box, the first wing box support tool being closer to a root end of the wing box than is the second wing box support tool and the third wing box support tool being closer to a tip end of the wing box than is the second wing box support tool, each of the first, second and third wing box support tools being configurable between a first state wherein it supports the wing box and obstructs the payload platform and a second state wherein it neither supports the wing box nor obstructs the payload platform; configuring the first, second and third wing box support tools so that the second and third wing box support tools support the wing box while the first wing box support tools does not; while the second and third wing box support tools are supporting the wing box, moving the first tractor vehicle from a position whereat the payload platform overlies a space between the root end of the wing box and the first wing box support tool to a position whereat the payload platform overlies a space between the first and second wing box support tools; after the preceding step has been performed, reconfiguring the first and second wing box support tools so that the first and third wing box support tools support the wing box while the second wing box support tools does not; and while the first and third wing box support tools are supporting the wing box, moving the first tractor vehicle from the position whereat the payload platform overlies a space between the first and second wing box support tools to a position whereat the payload platform overlies a space between the second and third wing box support tools. A fourth wing box support tool can be employed to facilitate passage of the payload platform from one side to the other side of the third wing box support tool.

A further aspect of the subject matter disclosed herein is an apparatus for scanning a wing box skin, comprising: a first tractor vehicle comprising a first frame, a plurality of wheels rotatably coupled to the first frame, a first coupling element, a first plurality of magnets supported by the first frame, a first drive wheel for driving the first tractor vehicle to move, and a first motor for driving rotation of the first drive wheel, the first motor being supported by the first frame; and a first payload platform comprising a second frame, a plurality of wheels rotatably coupled to the second frame, a second coupling element, a first maintenance tool supported by and movable relative to the second frame, and a first actuator for moving the first maintenance tool relative to the second frame, the first actuator being supported by the second frame, wherein first and second coupling elements are coupled to each other.

In accordance with one embodiment, the apparatus described in the preceding paragraph may further comprise a second tractor vehicle, the second tractor vehicle comprising a third frame, a plurality of wheels rotatably coupled to the third frame, a third coupling element, a second plurality of magnets supported by the third frame, a second drive wheel for driving the second tractor vehicle to move, and a second motor for driving rotation of the second drive wheel, the second motor being supported by the second frame, wherein the first payload platform further comprises a fourth coupling element, the third and fourth coupling elements being coupled to each other. The first coupling element is pivotable relative to the second coupling element, and the third coupling element is pivotable and slidable relative to the fourth coupling element.

In accordance with another embodiment, the apparatus described two paragraphs above may further comprise a second payload platform comprising a third frame, a plurality of wheels rotatably coupled to the third frame, a third coupling element, a second maintenance tool supported by and movable relative to the third frame, and a second actuator for moving the second maintenance tool relative to the third frame, the second actuator being supported by the third frame, wherein the first tractor vehicle further comprises a fourth coupling element, the third and fourth coupling elements being coupled to each other.

A further aspect of the subject matter disclosed herein is a system for performing a maintenance function on a wing box skin, comprising: (a) a hollow composite structure comprising first and second spars and first and second skins connected by the first and second spars; (b) a mobile platform comprising: (i) a chassis comprising first and second chassis parts coupled to each other, the first chassis part overlying a first portion of the first spar, each of the first and second chassis parts comprising a respective plurality of wheels in contact with the external surface of the first skin; (ii) a first drive wheel rotatably coupled to the first chassis part and in contact with the external surface of the first skin; (iii) a first actuator mounted to the first chassis part for causing the first drive wheel to rotate; (iv) a first plurality of magnets mounted to the first chassis part; and (v) a first maintenance tool slidably coupled to the second chassis part, the first maintenance tool being slidable along the second chassis part; and (vi) a second actuator mounted to the second chassis part for causing the first maintenance tool to slide along the second chassis part; (c) a first trailer vehicle disposed adjacent a first portion of an internal surface of the first skin and adjacent one side of the first spar, the first trailer vehicle comprising a second plurality of magnets, at least one magnet pole of the second plurality of magnets being magnetically coupled to a magnet pole of the first plurality of magnets through the first skin; and (d) a second trailer vehicle disposed adjacent a second portion of an internal surface of the first skin and adjacent another side of the first spar, the second trailer vehicle comprising a third plurality of magnets, at least one magnet pole of the third plurality of magnets being magnetically coupled to a magnet pole of the first plurality of magnets through the first skin, and at least one magnet pole of the third plurality of magnets being magnetically coupled to a magnet pole of the second plurality of magnets through the first spar, wherein the magnetically coupled mobile platform and first and second trailer vehicles move in unison when the drive wheel is rotated.

In cases where the first maintenance tool is an inspection unit, the mobile platform may further comprise means for measuring an X position and a Y position of the inspection unit, and the system further comprises a pulser/receiver unit operatively coupled to the inspection unit and to the first and second encoding means. The pulser/receiver unit is programmed to perform the following operations: sending control signals to the inspection unit; receiving scan data signals from the inspection unit; receiving X-Y position data signals from the measuring means; and correlating the scan data with the X-Y position data.

In accordance with another aspect, the system may further comprise: a plurality of motion script files containing sequences of motion commands and parameters respectively associated with a plurality of motion paths; and a computer system programmed to execute a sequence of commands in a selected one of plurality of motion scripts, the sequence of commands controlling operation of the first and second actuators to cause the first maintenance tool to move along a corresponding selected one of the motion paths in accordance with its associated parameters.

In accordance with one embodiment, the chassis further comprises a third chassis part coupled to the second chassis part, the third chassis part comprising a respective plurality of wheels in contact with the external surface of the first skin, the third chassis part overlying a portion of the second spar. In this embodiment, the mobile platform further comprises: a second drive wheel rotatably coupled to the third chassis part and in contact with the external surface of the first skin, the third chassis part being movable along a third motion path when the second drive wheel rotates while in contact with the external surface of the first skin; a second actuator mounted to the third chassis part for causing the second drive wheel to rotate; a fourth plurality of magnets mounted to the third chassis part; a third encoder for measuring a position of the third chassis part along the third motion path. In addition, the system further comprises: a third trailer vehicle disposed adjacent a third portion of an internal surface of the first skin and adjacent one side of the second spar, the third trailer vehicle comprising a fifth plurality of magnets, at least one magnet pole of the fifth plurality of magnets being magnetically coupled to a magnet pole of the fourth plurality of magnets through the first skin; and a fourth trailer vehicle disposed adjacent a fourth portion of an internal surface of the first skin and adjacent another side of the second spar, the second trailer vehicle comprising a sixth plurality of magnets, at least one magnet pole of the sixth plurality of magnets being magnetically coupled to a magnet pole of the fourth plurality of magnets through the first skin, and at least one magnet pole of the sixth plurality of magnets being magnetically coupled to a magnet pole of the fifth plurality of magnets through the second spar. In this embodiment, the first chassis part is pivotably coupled to the second chassis part, and the third chassis part is pivotably coupled and slidably coupled to the second chassis part.

In accordance with an alternative embodiment, the chassis further comprises a third chassis part coupled to the first chassis part, the third chassis part comprising a respective plurality of wheels in contact with the external surface of the first skin, the third chassis part overlying a second portion of the first spar. In this alternative embodiment, the mobile platform further comprises: a second maintenance tool slidably coupled to the third chassis part, the second maintenance tool being slidable along the third chassis part; and a third actuator mounted to the third chassis part for causing the second maintenance tool to slide along the third chassis part.

Other aspects are disclosed and claimed below.

BRIEF DESCRIPTION OF THE DRAWINGS

FIG. 10A shows an inspection scenario wherein the scanning apparatus is atop the top skin, while FIG. 10B shows an inspection scenario wherein the scanning apparatus is inverted and underneath the bottom skin.

FIGS. 14A and 14B show an inspection scenario wherein the scanning apparatus is atop the top skin.

FIGS. 15A through 15C are diagrams showing respective side views of configurable tools designed to support a wing box during non-destructive inspection using the systems disclosed herein. FIGS. 15A through 15C show three configurations which may occur during a configuration change sequence.

Reference will hereinafter be made to the drawings in which similar elements in different drawings bear the same reference numerals.

DETAILED DESCRIPTION

The maintenance tool-scanning mobile platform disclosed herein is designed for scanning a maintenance tool over an external surface of a skin of a hollow structure. As used herein, the term "maintenance tools" includes, but is not limited to, NDI units, drills, scarfers, grinders, fasteners, appliqué applicators, ply mappers, and depainting, cleaning and painting tools. For the purpose of illustration, various embodiments will be described in which the maintenance tool is an NDI unit (e.g., an array of ultrasonic transducers).

Figure 1:
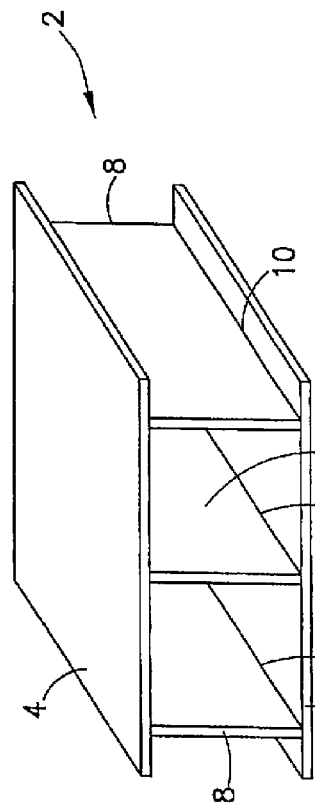
FIG. 1 is a diagram showing an orthographic view of a portion of a generalized horizontal stabilizer of an airplane having top and bottom skins or panels connected by a plurality of spars.

In accordance with the embodiments disclosed herein, ultrasonic NDI sensors are used to inspect a hollow composite structure, such as an integrally stiffened wing box for an aircraft (e.g., a horizontal stabilizer). A portion of a generalized integrally stiffened wing box 2 for an aircraft is depicted in FIG. 1. The depicted integrally stiffened wing box comprises a top skin 4 and a bottom skin 6 connected by a plurality of internal vertical support elements, hereinafter referred to as "spars". Each spar comprises a web 8 and respective pairs of filleted join regions 10 (also called "spar radii"), which connect the spar web 8 to the top and bottom skins. As used herein, the terms "top skin" and "bottom skin" refer to the relative positions of two skins of a wing box when the wing box is being inspected, not when the wing box is installed on an airplane (i.e., a wing box may be inverted for inspection).

In accordance with the system disclosed in U.S. patent application Ser. No. 13/534,014 (the contents of which are incorporated by reference herein in their entirety), an NDI sensor (e.g., a linear ultrasonic transducer array) is transported down the length of a tunnel through the interior of the composite structure. For this type of inspection, the sensor is carried by a trailer vehicle (not shown in FIG. 1) placed inside the hollow structure 2. This trailer vehicle can be characterized as being "active" in the sense that equipment it carries is actively performing a scanning function. For some types of inspection applications, the sensor needs to be acoustically coupled to each surface being inspected while an automated external tractor vehicle (also not shown in FIG. 1) moves the trailer vehicle along that surface in a region of interest. In the case of ultrasonic inspection, acoustic coupling is provided by a column of water that flows between the sensor and the inspected part.

In FIG. 1, portions of the interior surfaces of the part which need to be inspected can be seen. Each spar needs to have web 8 and all four filleted join regions 10 inspected. This is a challenging inspection as each cavity is essentially a long rectangular tunnel that decreases in cross section as one moves from root to tip. A system designed for spar inspection using scanning apparatus placed inside the wing box is disclosed in U.S. patent application Ser. No. 13/534,014. In contrast, this disclosure is directed to inspecting the top and bottom skins 4 and 6 using scanning apparatus placed outside the wing box.

The top and bottom skins of a wing box can be inspected by a transporter system comprising magnetically coupled external and internal vehicles. The basic principle of operation of such magnetically coupled vehicles will now be described with reference to FIGS. 2 and 3, which side and end views respectively of an external motorized and computer-controlled tractor 12 magnetically coupled to an internal trailer 14 disposed inside a wing box. Also, there is an internal trailer 16 (see FIG. 3) on the opposite side of the spar that is magnetically coupled through the spar to trailer 14 and also magnetically coupled through the skin to the tractor 12. This three-part system gives a very stable system for positioning and moving an NDI sensor unit, such as a unit comprising an array of ultrasonic transducers configured to scan in a scan plane.

Figure 2:
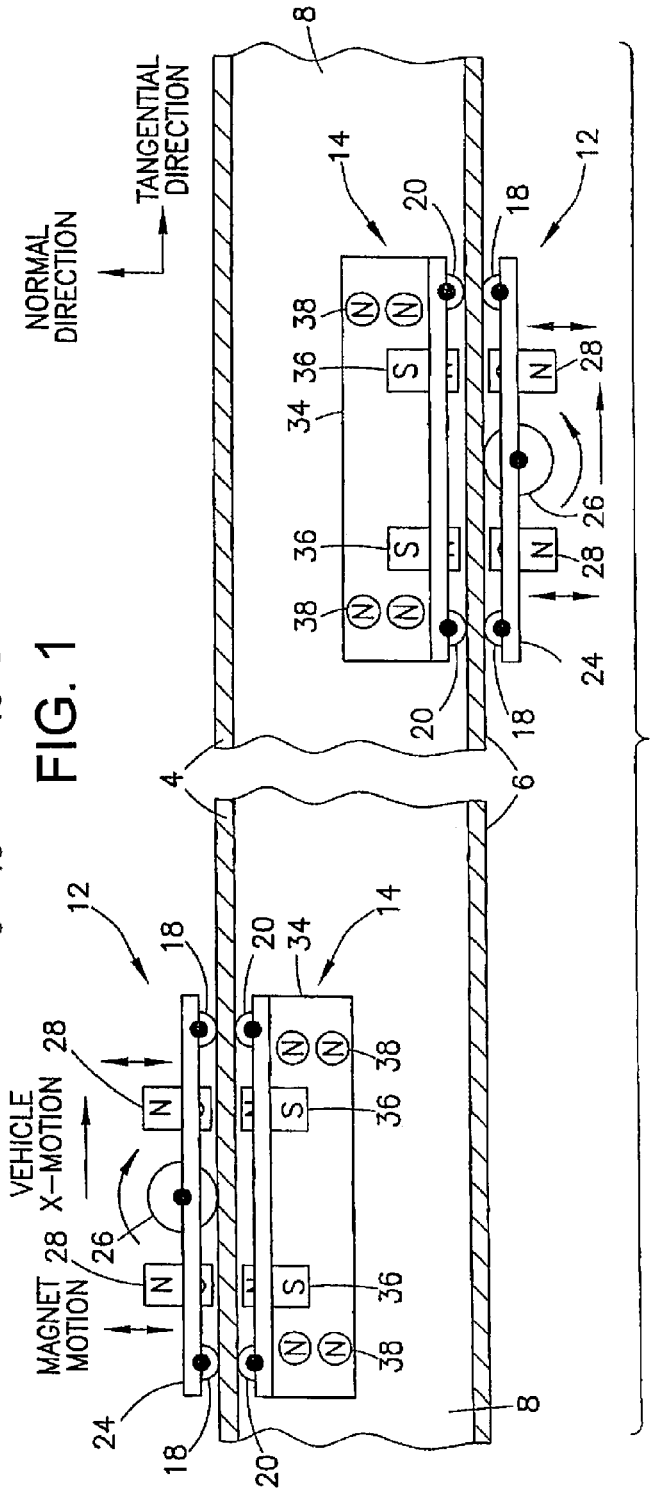
FIG. 2 is a diagram showing side views of a tractor-trailer configuration having means for adaptive magnetic coupling. A second trailer vehicle is not visible. The left-hand side of FIG. 2 shows an inspection scenario wherein the trailer vehicles are inverted, while the right-hand side shows an inspection scenario wherein the tractor vehicle is inverted.
Figure 3:
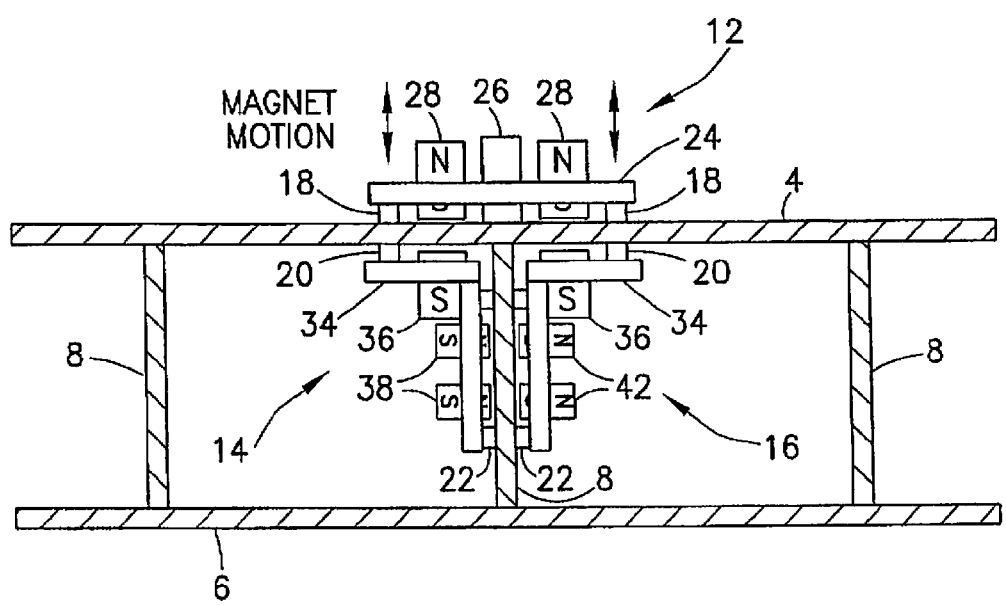
FIG. 3 is a diagram showing an end view of the tractor-trailer configuration depicted on the left-hand side of FIG. 2 (with respective inverted trailer vehicles disposed on opposing sides of a spar).

FIG. 2 shows side views of a tractor-trailer configuration in accordance with one embodiment in two different inspection situations (motor actuators are not shown). The automated NDI inspection system comprises a traction-motor powered tractor vehicle 12, which rides on the external surface of top skin 4 or bottom skin 6 of wing box 2, and a pair of trailer vehicles (only trailer vehicle 14 is visible in FIG. 2, the other being hidden behind a spar web 8), which ride along an internal surface of the top or bottom skin. The left-hand side of FIG. 2 shows an inspection scenario wherein the tractor vehicle 12 is outside the wing box in a non-inverted position while the trailer vehicles are inside the wing box in inverted positions; the right-hand side of FIG. 2 shows an inspection scenario wherein the tractor vehicle 12 is outside the wing box in an inverted position while the trailer vehicles are inside the wing box in non-inverted positions. FIG. 3 shows an end view of the tractor-trailer configuration depicted on the left-hand side of FIG. 2, with inverted trailer vehicles 14 and 16 disposed on opposite sides of a spar.

In the inspection scenario depicted in FIG. 3 (and the left-hand side of FIG. 2), idler wheels 18 of tractor vehicle 12 contact and roll on the external surface of top skin 4 while vertical idler wheels 20 of inverted trailer vehicles 14 and 16 (only one such idler wheel is visible in FIG. 3 for each trailer vehicle) contact and roll on the internal surface of top skin 4, and the horizontal idler wheels 22 roll on the spar surface. The right-hand side of FIG. 2 show an alternative situation wherein idler wheels 18 of the inverted tractor vehicle 12 contact and roll on the external surface of bottom skin 6 while vertical idler wheels 20 of trailer vehicle 14 (and also idler wheels of trailer vehicle 16 not visible in FIG. 2) contact and roll on the internal surface of bottom skin 6, and the horizontal idler wheels 22 roll on the spar surface.

In accordance with the embodiment partly depicted in FIGS. 2 and 3, the tractor vehicle 12 comprises a frame 24. Four idler wheels 18 (only two of which are visible in each of FIGS. 2 and 3) are rotatably mounted to frame 24 in a conventional manner. (Alternative embodiments may include more idler wheels.) The idler wheels 18 may be made of plastic and have smooth contact surfaces. Tractor vehicle motion is enabled by driving a drive wheel 26 (also rotatably mounted to frame 24) to rotate. Drive wheel 26 is coupled to a motor via a transmission (neither are shown in FIGS. 2 and 3). The drive wheel 26 is positioned on the frame 24 so that it is in frictional contact with skin 4 or 6 when idler wheels 18 are in contact with the same skin. The drive wheel 26 can be made of synthetic rubber material. The surface of the drive wheel may have a tread pattern. In addition, the tractor vehicle 12 carries multiple permanent magnets 28. Each permanent magnet 28 has North and South poles, respectively indicated by letters "N" and "S" in the drawings.

Still referring to FIGS. 2 and 3, each trailer vehicle 14, 16 is comprised of a respective frame 34. For each trailer vehicle, two vertical idler wheels 20 (only one of which is visible in FIG. 3) and four horizontal idler wheels 22 (only two of which are visible in FIG. 3) are rotatably mounted to frame 34 in a conventional manner. (Alternative embodiments may include more idler wheels.) Each trailer vehicle 14, 16 carries multiple vertically mounted permanent magnets 36, the North poles of which are magnetically coupled to the South poles of confronting permanent magnets 28 carried by the tractor vehicle 12. In the design shown in FIGS. 2 and 3, each trailer has two vertically mounted permanent magnets 36, but other designs may use different configurations. The positions and pole orientations of the magnets may have other configurations as long as the N-S pairing and relative alignment of the magnets between the tractor and trailer are preserved.

As seen in FIG. 3, in addition to being magnetically coupled to the tractor vehicle 12, the trailer vehicles 14 and 16 are magnetically coupled to each other using additional sets of permanent magnets 38 and 42. As seen in FIG. 2, trailer vehicle 14 carries four horizontally mounted permanent magnets 38. Trailer vehicle 16 also carries four horizontally mounted permanent magnets 42 (only two of which are visible in FIG. 3), the poles of which are respectively magnetically coupled to opposing poles of the permanent magnets 38 on trailer vehicle 14. This magnetic coupling produces an attraction force that holds idler wheels 22 of trailer vehicles 14 and 16 in contact with opposing surfaces of an intervening spar web 8 (shown in FIG. 3).

FIGS. 2 and 3 show the basic principle of placing magnetically coupled vehicles on the exterior and in the interior of a hollow structure comprising top and bottom skins connected by at least two spars. That principle can be applied when scanning the surface skins of a hollow structure using an externally mounted NDI sensor unit. In accordance with some embodiments, the NDI sensor unit may comprise a linear array of ultrasonic transducers which can be acoustically coupled to the external surface of the skin being inspected. For example, the inspected region may be covered with a continuous stream of water to acoustically couple the ultrasonic transducers to a top or bottom skin. Magnetically coupled systems are well suited for operation with water in the environment.

In accordance with some embodiments disclosed below, an external mobile platform may comprise two drive tractor vehicles pivotably coupled to front and/or rear payload platforms (e.g., a crossbar bridge), each tractor vehicle being magnetically coupled to a respective pair of passive trailer vehicles disposed inside the hollow structure. In accordance with other embodiments disclosed below, an external mobile platform may comprise a single drive tractor vehicle coupled to front and/or rear payload platforms (e.g., trailer vehicles).

As the tractor vehicle is driven to travel along a desired path on the outer surface of the top or bottom skin, it pulls and/or pushes one or more external payload platforms. Each externally mounted tractor vehicle is magnetically coupled to a respective pair of passive trailers disposed inside the wing box on opposing sides of a spar. The magnetic coupling system described with reference to FIGS. 2 and 3 keeps the inverted vehicles in contact with the surface skin which they ride on. The internal passive trailers roll along the surfaces of the spar, which allows the scanning system to take advantage of the internal structure of the wing box as a guide to track properly along the surface skin.

Each tractor vehicle can be provided with a capability to vary the amount of magnetic coupling force by physically moving its magnets up or down using motors that are under computer control. This allows the apparatus to match the magnetic coupling force to the thickness of the part being inspected. In this case, as the part thickness varies along the length of the part, the magnetic coupling force is dynamically adjusted under computer control to reflect this. An externally mounted payload trailer vehicle may be provided with the same capability. A feedback sensor is needed to provide information required by the control computer to adjust the magnet separation distance as the skin thickness varies. One sensor option is a wheel rotation encoder rotatably mounted to the frame of one of the trailer vehicles to provide displacement from a specified starting point along the length of the wing box (or other structure being inspected). This position information, along with predetermined data about the thickness of the skin (either from a CAD model or measured directly), can be used to determine the amount of displacement needed for the movable magnet units on the tractor or on an external payload platform. By knowing the locations of each of the magnetic coupling units relative to the sensor, the desired separation at each of the magnets can be determined. FIGS. 2 and 3 do not show the means for automatically adapting to the variable thickness of the intervening skin or panel (i.e., top skin 4 or bottom skin 6) by raising or lowering the magnets (which magnet motion is indicated by double-headed arrows in FIGS. 2 and 3) on the tractor vehicle as it moves along the structure being inspected. Further details concerning the trailer-tractor configuration depicted in FIGS. 2 and 3 and other embodiments are disclosed in U.S. patent application Ser. No. 13/313,267, the disclosure of which is incorporated by reference herein in its entirety.

The basic concept of the tractor/trailer transporter system described above can be adapted to provide an alternative solution for NDI scanning of wing box surface skins that is compatible with the process for scanning of the wing box interior surfaces disclosed in U.S. patent application Ser. No. 13/534,014. The system consists of smaller components that can be setup in new locations without the need for construction of extensive infrastructure. The entire NDI skin scanning system could be shipped in cases. The only needed local infrastructure would be water, air, power and support structure for the horizontal stabilizer during inspection.

The apparatus and methods disclosed herein enable maintenance tool scanning of surface skins using a magnetically coupled crawler vehicle. In cases where the maintenance tool is a sensor that needs to contact the scanned surface, the scanning mechanism may comprise a sensor attachment mounted in such a way as to provide compliance between the sensor and the scanned surface. A further feature is a multi-configuration support tool that enables scanning of the bottom surface skin of a wing box. The scanning method includes motion planning that enables the collections of the scan strips on the top and bottom skins without turning the wing box over.

The skin scanning system comprises at least one drive tractor platform, e.g., a tractor vehicle, and at least one payload platform, e.g., a trailer vehicle coupled to a tractor vehicle or a crossbar bridge coupled to a pair of tractor vehicles, that is pushed or pulled by the tractor. The tractor and payload platforms are coupled to each other, which coupling may be a mechanical or magnetic coupling. The tractor vehicle may comprise multiple motors, including a motor for driving a main drive wheel and motors for controlling the adaptive magnetic coupling system (which moves the coupling magnets in order to maintain required magnetic attraction force for variable surface thickness) onboard the tractor vehicle. The payload platform may comprise multiple motors, including a motor for moving the payload (e.g., an NDI sensor) in a lateral direction, i.e., generally transverse to the direction of motion of the tractor, and in some embodiments, motors for controlling an adaptive magnetic coupling system onboard the payload platform. The payload platform may also have one or more rotation wheel encoders to measure distance traveled in the X direction due to motion generated by the tractor drive motor(s), and the payload platform may have another rotational encoder to measure the distance that the sensor has moved in the Y direction due to motion generated by the payload motion motor. All of the motors carried by the external tractor and payload platforms are computer controlled. In contrast, the trailer vehicles inside the wing box (e.g., a horizontal stabilizer) may be passive components. The connections to a computer from the vehicles are through a communication cable that is controlled by a separate cable management device, the structure of which is disclosed in U.S. patent application Ser. No. 13/534,014.

Figure 4:
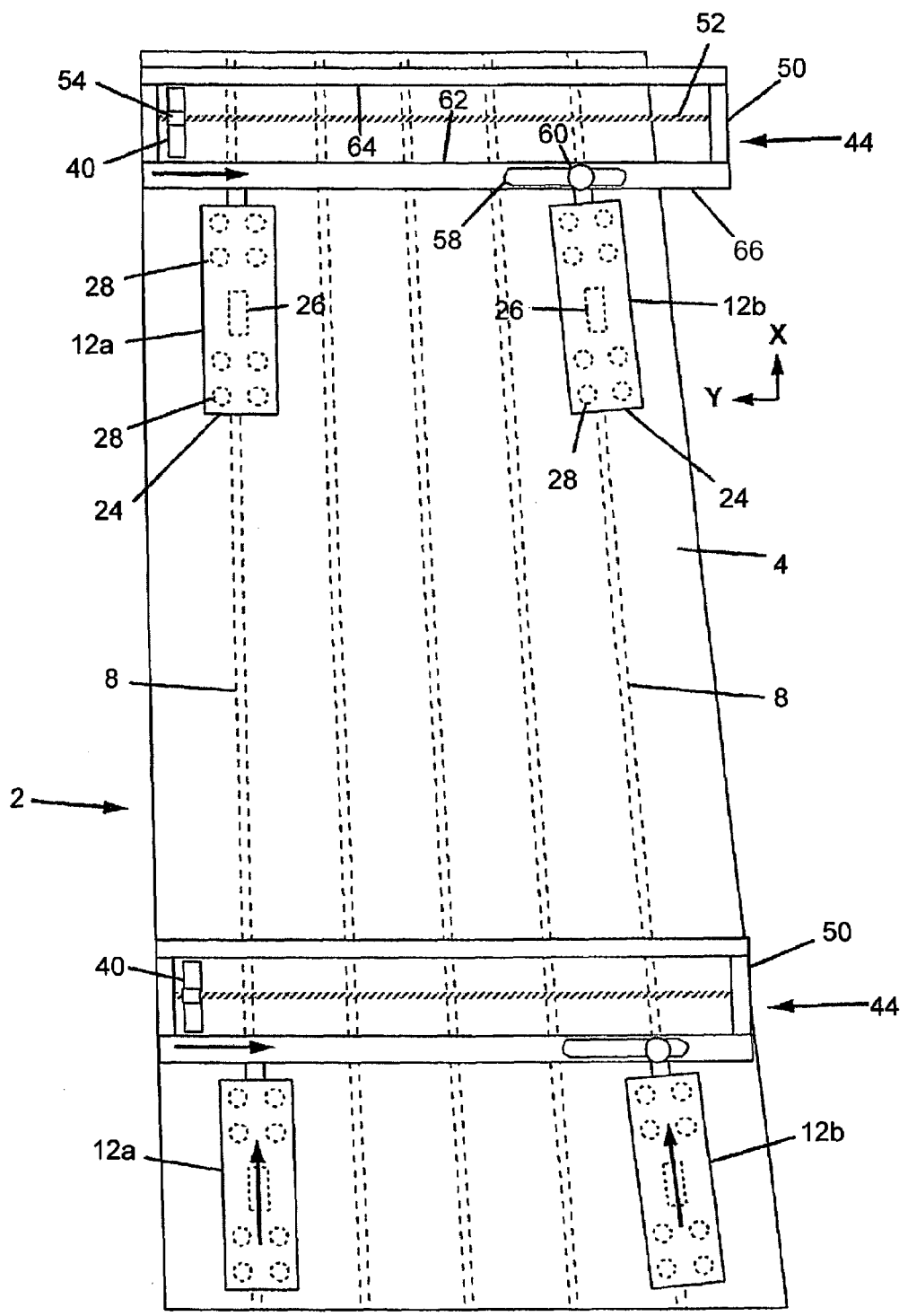
FIG. 4 is a diagram showing a top view of an external skin scanning apparatus atop a surface skin of a wing box, the apparatus having a double-tractor configuration in accordance with one embodiment. The apparatus is shown in two possible positions.

FIG. 4 shows a top view of an external skin scanning apparatus atop a surface skin of a wing box 2, the apparatus having a double-tractor transporter configuration in accordance with one embodiment. The apparatus is shown in two possible positions. The double-tractor transporter configuration for scanning a wing box skin 4 uses two drive tractor units 12a, 12b that are similar in design to the tractor previously described with reference to FIGS. 2 and 3. The tractor vehicles 12a, 12b ride on the exterior skin surface of the wing box. The tractors are magnetically coupled to respective pairs of passive trailers (not visible in FIG. 4, but see FIG. 3) on the internal surface of skin 4 and spars 8 of the wing box 2. They are connected together by a payload platform 44 comprising a frame 50 that may ride on rolling elements, e.g., wheels (not visible in FIG. 4). Alternately, the frame may be attached by coupling elements directly to the tractor (such as a cantilevered support arrangement). Frame 50 comprises a crossbar 66 that bridges the two tractor vehicles 12a, 12b. The payload platform 44 further comprises an NDI sensor array 40 (e.g., a linear array of ultrasonic transducers) attached to a drive nut 54. The drive nut 54 is threadably coupled to a lead screw 52 that is rotatably coupled to frame 50. The scan plane of NDI sensor array 40 is oriented perpendicular to the axis of lead screw 52. The payload platform 44 further comprises alignment guide elements 62 and 64 that guide the NDI sensor array 40 along a linear path. The NDI sensor array 40 is housed in a shoe (not shown) that slides along the alignment guide elements 62, 64. The payload platform 44 further comprises a motor (e.g., a stepper motor) (not shown in FIG. 4) which drives rotation of the lead screw 52. In response to lead screw rotation, the NDI sensor array 40 will translate along the length of frame 50, i.e., in a lateral direction relative to the spar 8 underlying the tractor vehicle 12a. The NDI sensor array 40 is preferably mounted via a mechanism (e.g., a spring-loaded shoe) that provides a sufficient amount of vertical compliance to enable the array to stay in contact with a curved aerodynamic surface of a horizontal stabilizer.

The payload platform 44 and the tractor vehicles 12a, 12b are coupled together to form a chassis that is movable in a spanwise direction along a wing box for an airplane. For scanning a surface skin of a horizontal stabilizer, the tractor vehicles 12a, 12b cannot be rigidly coupled by the crossbar 66 since they have to stay on the surface of skin 4 and that surface is not flat. In addition, the tractor motions will not be parallel, since the spars 8 inside the horizontal stabilizer are not parallel. In the setup shown in FIG. 4, the tractor-platform couplings allow pivoting between the two tractors, as well as extension and contraction. Another option is to have the tractors ride on one path on the crossbar and the sensor array ride on another. The system has one tractor to be coupled to the crossbar 66 with a sliding and rotating joint, while the other tractor is coupled by a rotating joint. In the embodiment shown in FIG. 4, the tractor vehicle 12a (i.e., the first chassis part) is pivotably coupled to the payload platform 44 (i.e., the second chassis part) by a hitch type of coupling mechanism (e.g., a ball joint) (not visible in FIG. 4). In addition, the tractor vehicle 12b (i.e., the third chassis part) is pivotably coupled and slidably coupled to the payload platform 44. The mechanism for coupling tractor vehicle 12b to payload platform 44 comprises a ball joint (not visible in FIG. 4) connected to a pin 60 which slides freely in a slot 58 formed in crossbar 66 of frame 50.

In accordance with an alternative embodiment in which the frame has a cantilevered configuration, a joint with only two degrees of freedom (such as two revolute joints) can be employed instead of a ball joint.

The magnetic couplings between the external tractor vehicles and the internal passive trailer vehicles, with respective skin-spar joints therebetween, couples the trailer vehicles to the wing box. Since the payload platform is coupled to and its motion is constrained by the trailer vehicles, the coupling of the trailer vehicles to respective spars has the effect of coupling the payload platform to the wing box. Thus the payload platform does not require means for gripping parts (e.g., the leading and trailing edges) of the wing box.

Figure 5:
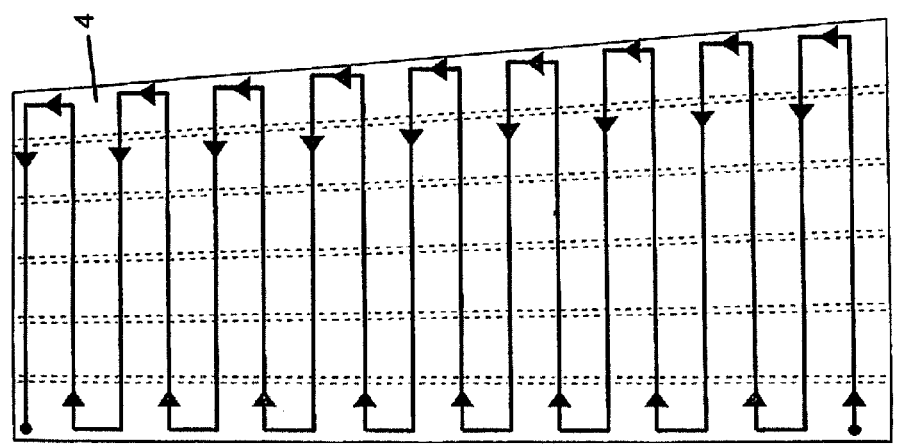
FIG. 5 is a diagram showing a top view of a wing box skin with a potential scan path plan (assuming installation of a runoff component at the wide end of the wing box) depicted as a serpentine line superimposed on the skin, which serpentine line represents a path of travel of a point on an NDI sensor during scanning of the skin using the apparatus depicted in FIG. 4.

For the usage setup shown in FIG. 4, the two tractors 12a, 12b and the payload platform 44 can be positioned on one end of the horizontal stabilizer, and the process is started by moving the NDI sensor array 40 in the Y direction all the way from one edge of the wing box to the other edge. After the array has been stopped, both tractors are moved simultaneously a few inches ahead. Then the Y direction scan is repeated, except that the array is now moved in the opposite direction. Again the array is stopped and then the tractors are moved another few inches ahead. This scanning process can be repeated until the entire surface skin 4 has been scanned. The path trace for this scanning mode is shown in FIG. 5.

Figure 7:
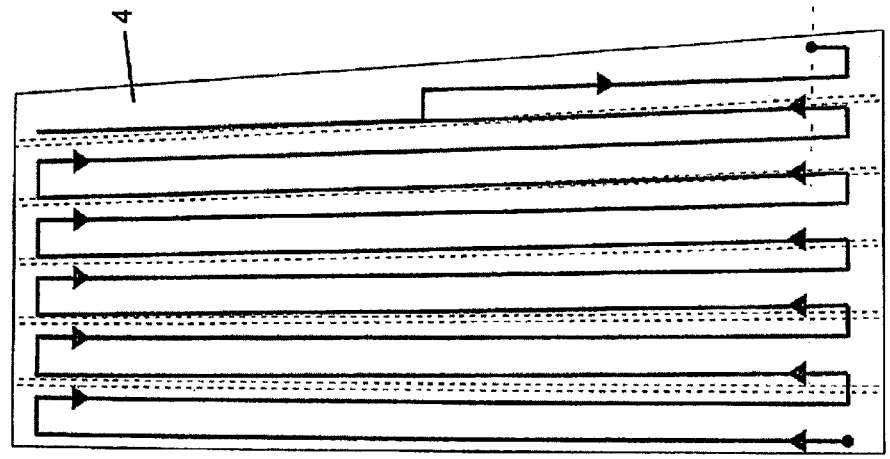
FIG. 7 is a diagram showing a top view of a wing box skin with a potential scan path plan (assuming installation of a runoff component at the wide end of the wing box) depicted as a serpentine line superimposed on the skin, which serpentine line represents a path of travel of a point on an NDI sensor during scanning of the skin using the apparatus depicted in FIG. 6.
Figure 6:
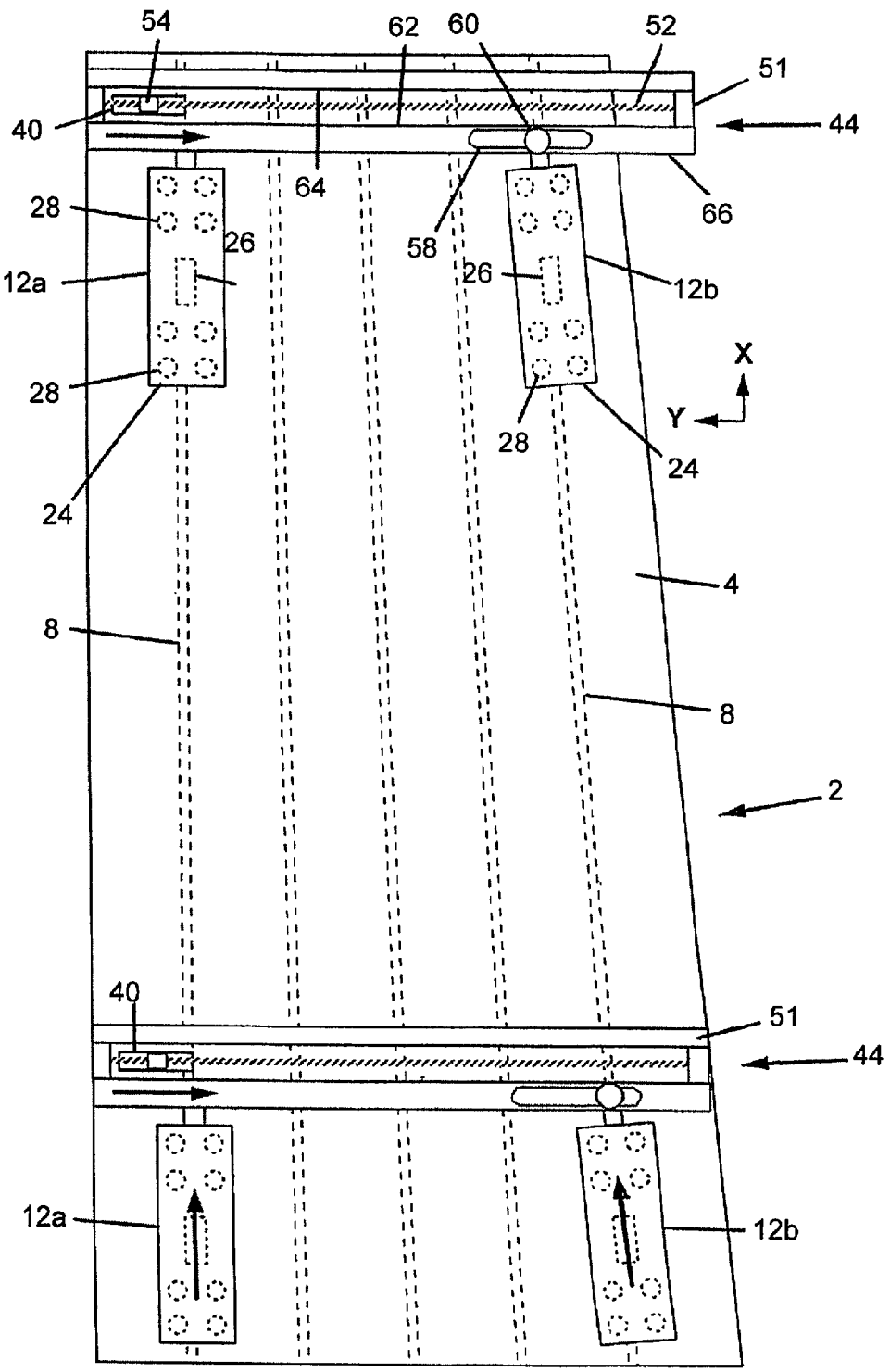
FIG. 6 is a diagram showing a top view of an external skin scanning apparatus atop a surface skin of a wing box, the apparatus having a double-tractor configuration in accordance with another embodiment. The apparatus is shown in two possible positions.

In accordance with a variation of the embodiment shown in FIG. 4, the NDI sensor array 40 can be rotated 90 degrees (i.e., oriented parallel to the axis of lead screw 52), as shown in FIG. 6. A frame 51 (which can be narrower than frame 50 seen in FIG. 4 due to the change in array orientation) has a crossbar 66 that bridges two tractor vehicles 12a, 12b. In this case the scanning process is started by indexing the NDI sensor array 40 to the starting position along the frame 51, i.e., in the Y direction. Then the tractors 12a, 12b are moved all the way along the length of respective spars 8 for each Y direction index position. The path trace for a potential path plan for this scanning mode is shown in FIG. 7.

In the examples shown in FIGS. 4 and 6, when the NDI sensor array 40 cannot overlie the marginal strip adjacent one end of wing box 2 because the transporter (i.e., tractor vehicle and magnetically coupled internal trailer vehicles) has reached that end and can travel no further, a run-on/run-off component can be attached to the end of the wing box, which component is configured to enable the transporter to travel beyond (i.e., run-off) that end of the wing box. The same run-on/run-off component allows scanning to start at the same end of the wing box, in which case the transporter mechanisms runs onto the wing box from the run-on/run-off component. A pair of run-on/run-off components (i.e., each component can serve either function depending on whether the trailer vehicle is leading or trailing the payload platform) can be used to allow the externally mounted tractor vehicle and the internally mounted passive trailer vehicles to start partially off of or run partially off of either end of the wing box. These components will be respectively attached to the start and end positions and will allow the more centrally positioned NDI sensor array to cover the entire length of the wing box skin. These run-on/run-off components (which may be made of plastic or composite material) are sized and shaped to match the particular wing box being inspected and are different for the root and tip ends of the wing box. They may be clamped or taped in place.

Figure 8:
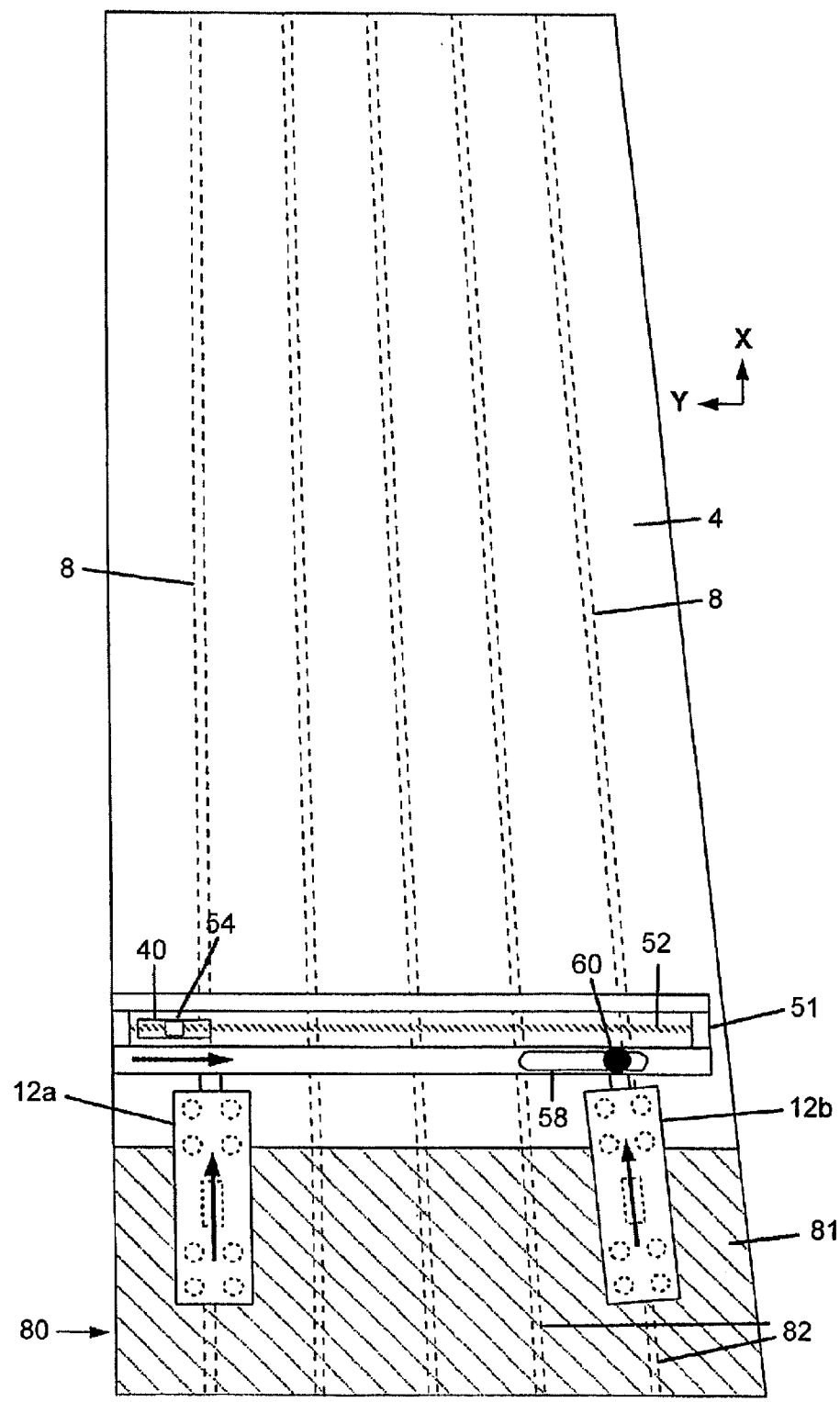
FIG. 8 is a diagram showing a top view of the external skin scanning apparatus depicted in FIG. 6, wherein the trailer vehicles are supported by a run-on component attached to the root end of the wing box.

FIG. 8 is a top view of the external skin scanning apparatus depicted in FIG. 6, wherein the tractor vehicles 12a and 12b are supported by a run-on/run-off component 80 that has been attached to the root end of a wing box. In this implementation, run-on/run-off component 80 comprises a top skin 81, a bottom skin (not visible in FIG. 8), and a multiplicity of spars 82 which respectively align with the spars and skins of the wing box. This enables each tractor vehicle 12a, 12b and its associated pair of internal passive trailer vehicles (not visible in FIG. 8) to transition smoothly from the wing box to the run-on/run-off component 80 (or vice versa) while maintaining their magnetic coupling to each other.

Figure 9:
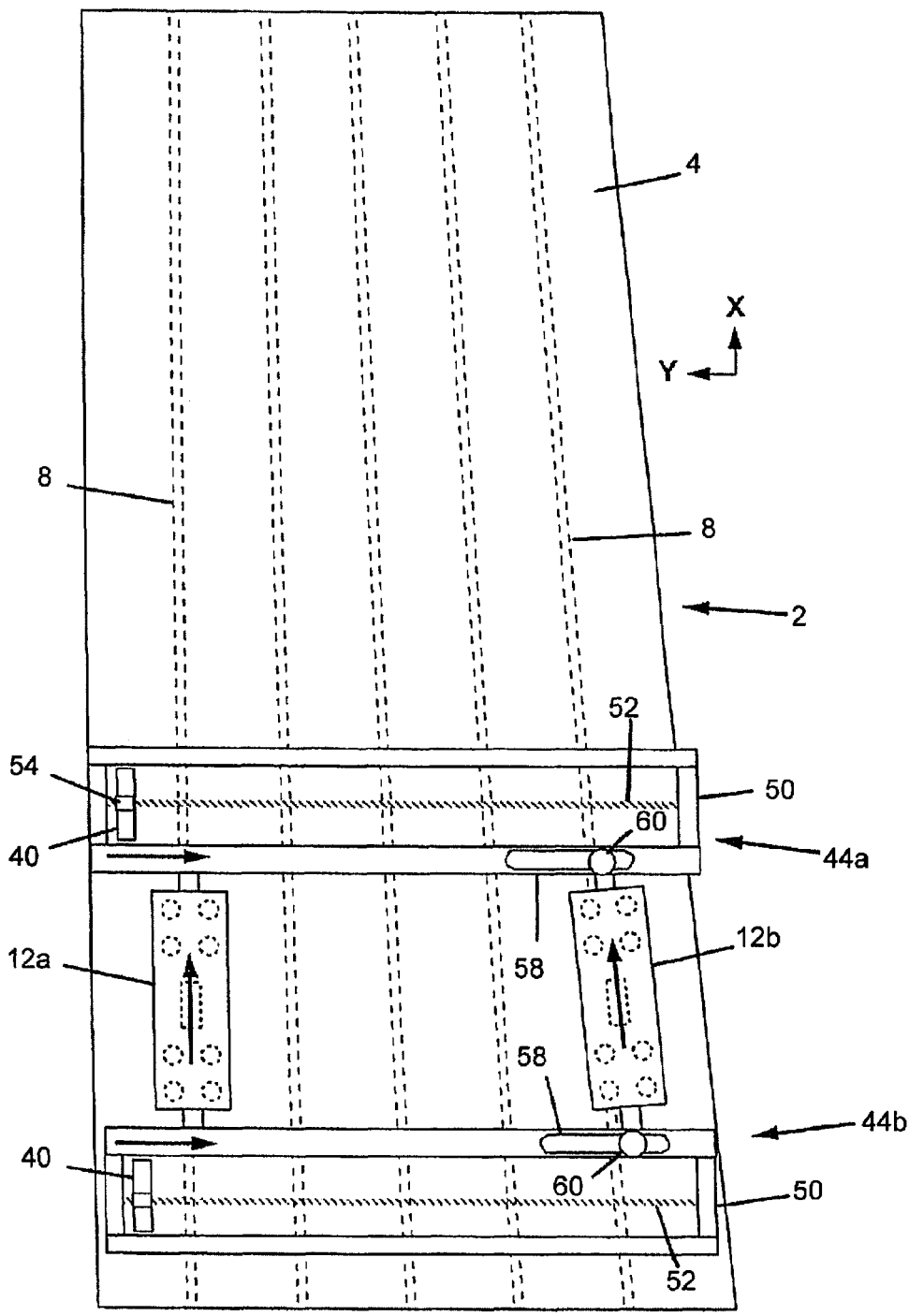
FIG. 9 is a diagram showing a top view of an external skin scanning apparatus atop a surface skin, the apparatus comprising two tractors pushing/pulling two crossbar bridges carrying respective NDI sensor units in accordance with a further embodiment.

FIG. 9 shows a top view of an external skin scanning apparatus in accordance with a variation of the embodiment shown in FIG. 4. This apparatus has front and rear payload platforms 44a and 44b coupled to front and read ends respectively of two tractor vehicles 12a, 12b. In the scenario depicted in FIG. 9, the tractor vehicles are traveling in the direction indicated by the arrows, in which case the tractors are pushing payload platform 44a and pulling payload platform 44b. Each payload platform 44a, 44b shown in FIG. 9 has a construction similar to that of payload platform 44 previously described with reference to FIG. 4, which description shall not be repeated here for the sake of brevity. One difference is that the frame 50 for payload platform 44a can be shorter in length than frame 50 of payload platform 44b due to the narrowing of the width of the skin as the apparatus moves toward the tip end of the wing box. Another difference is that the slots 60 of the respective frames 50 of payload platforms 44a, 44b are offset due to the fact that the spars 8 are converging, not parallel, as they extend from the root end to the tip end.

The apparatus shown in FIG. 9 is equipped with front and rear NDI sensor units 40 which can be operated independently. When payload platform 44b overlies the lateral marginal strip of skin surface adjacent the root end of the wing box, its NDI sensor unit 40 can inspect that strip without using a run-on/run-off component. Likewise when payload platform 44a overlies the lateral marginal strip of skin surface adjacent the tip end of the wing box, its NDI sensor unit 40 can inspect that strip without using a run-on/run-off component. The front and rear scanning units can be operated with synchronized motions in the path plan that involves moving the tractor to the appropriate positions to avoid overlap of the front and rear scans. This type of path plan may include scan groups that are the length of the spacing between the front and rear platforms, or it may include interlacing of the front and rear scan strips.

Figure 10:
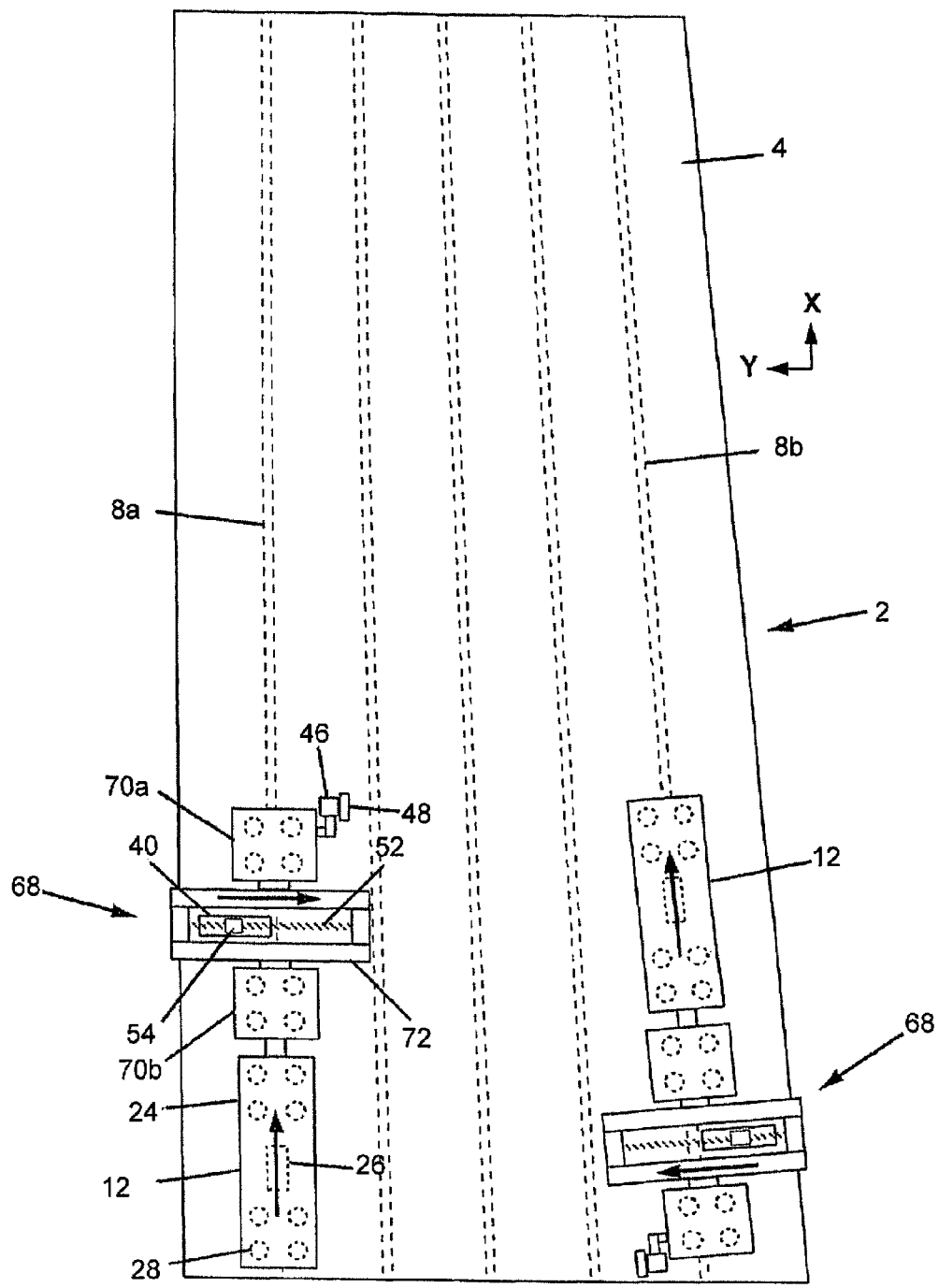
FIG. 10 is a diagram showing a top view of an external skin scanning apparatus atop a surface skin of a wing box, the apparatus comprising a single tractor coupled to a single NDI scanner trailer in accordance with yet another embodiment. The apparatus is shown in two possible positions and two possible operational modes (i.e., push and pull modes).

FIG. 10 shows a top view of an external skin scanning apparatus atop a surface skin of a wing box 2, the apparatus having a single-tractor transporter configuration in accordance with a further embodiment. The apparatus is shown in two possible positions. The single-tractor transporter configuration for scanning a wing box skin 4 comprises a drive tractor unit 12, similar in design to the tractor previously described with reference to FIGS. 2 and 3, coupled to an NDI scanner trailer vehicle 68.

The NDI scanner trailer vehicle 68 comprises an NDI sensor array 40 (e.g., a linear array of ultrasonic transducers) carried by a frame. The frame comprises first and second rolling frame parts 70a, 70b rigidly connected by a central frame part 72. A rotation encoder 46 may be mounted to the frame of NDI scanner trailer vehicle 68. In the implementation shown in FIG. 10, the rotation encoder 46 is mounted to the first rolling frame part 70a. An encoder wheel 48 is coupled to the rotation encoder 46. The rotation encoder outputs a respective pulse for each incremental angular rotation by encoder wheel 48 during travel of NDI scanner trailer vehicle 68 along a spar, providing an indication of the X position of the NDI sensor array 40. Similarly, a lead screw encoder (not shown in FIG. 10) can provide pulses indicating the Y position of the NDI sensor array 40 in a well-known manner.

The NDI sensor array 40 is slidably coupled to the central frame part 72, the latter comprising alignment guide elements (as previously described) that guide the NDI sensor array 40 along a linear path. The NDI sensor array 40 is coupled to a drive nut 54, which is threadably coupled to a lead screw 52 that is rotatably coupled to central frame part 72. In the example depicted in FIG. 10, the scan plane of the NDI sensor array 40 is oriented parallel to the axis of lead screw 52. Alternatively, the scan plane could be perpendicular to the lead screw (as seen in FIG. 4). The NDI scanner trailer vehicle 68 further comprises a motor (e.g., a stepper motor) (not shown in FIG. 10) which drives rotation of the lead screw 52. In response to lead screw rotation, the NDI sensor array 40 will translate along the length of central frame part 72, i.e., in a lateral direction relative to the spar underlying the tractor vehicle 12. The NDI sensor array 40 is preferably mounted via a mechanism (e.g., a spring-loaded shoe) that provides a sufficient amount of vertical compliance to enable the array to stay in contact with a curved aerodynamic surface of a horizontal stabilizer.

Figure 10A:
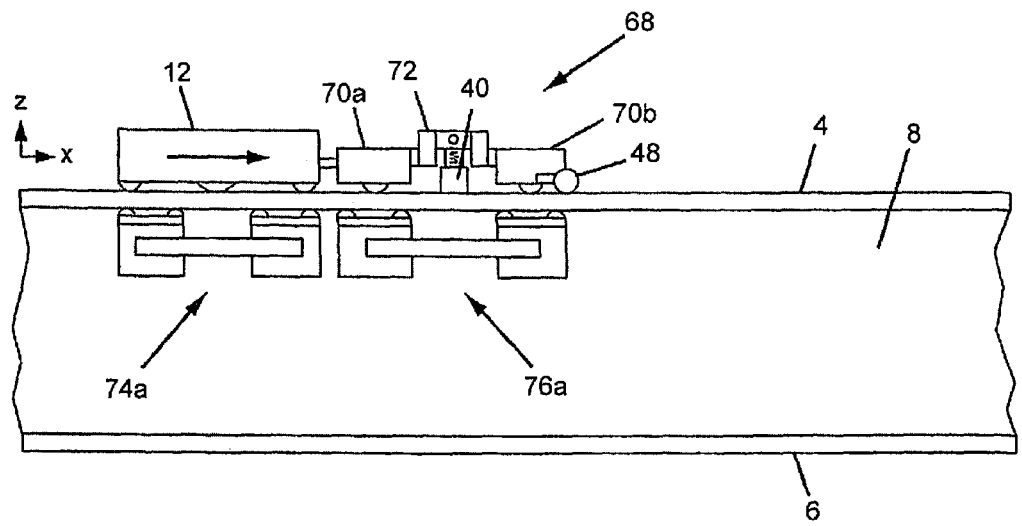
FIGS. 10A and 10B are diagrams showing side views of a configuration in which a scanning apparatus of the type shown in FIG. 10 is magnetically coupled to respective sets of passive trailer vehicles disposed on opposing sides of a spar and magnetically coupled to each other. The second set of passive trailer vehicles (disposed behind spar web 8) is not visible in either FIG. 10A or FIG. 10B.
Figure 10B:
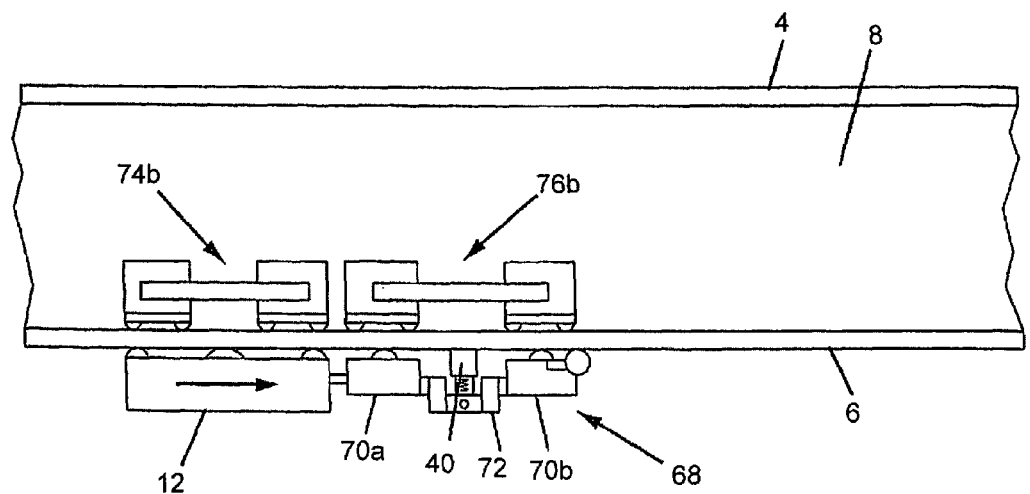

As shown in FIGS. 10A and 10B, the tractor vehicle 12 and NDI scanner trailer vehicle 68 can ride on either the exterior surface of top skin 4 or the exterior surface of bottom skin 6. In the latter case, the tractor vehicle 12 and NDI scanner trailer vehicle 68 will be inverted. The tractor vehicle 12 and NDI scanner trailer vehicle 68 are magnetically coupled to respective pairs of internal passive trailer vehicles. Each pair of internal passive trailer vehicles ride on the interior surface of the intervening skin and on opposing sides of a spar 8. Two internal passive trailer vehicles 74a and 76b are visible in FIG. 10A; the other two internal passive trailer vehicles 74b and 76b are visible in FIG. 10B. The internal passive trailer vehicles 74a,b are magnetically coupled to each other through a spar 8, as are internal passive trailer vehicles 76a,b.

The tractor-trailer combination shown in FIG. 10 can be placed at discrete positions along the width of the wing box associated with the locations of the respective interior spars. In the scenario depicted on the left-hand side of FIG. 10, the tractor vehicle 12 pushes the NDI scanner trailer vehicle 68 along a path dictated by spar 8a, which guides the internal passive trailer vehicles. Similarly, in the scenario depicted on the right-hand side of FIG. 10, the tractor vehicle 12 pulls the NDI scanner trailer vehicle 68 along a path dictated by spar 8b, which guides the internal passive trailer vehicles.

Figure 11:
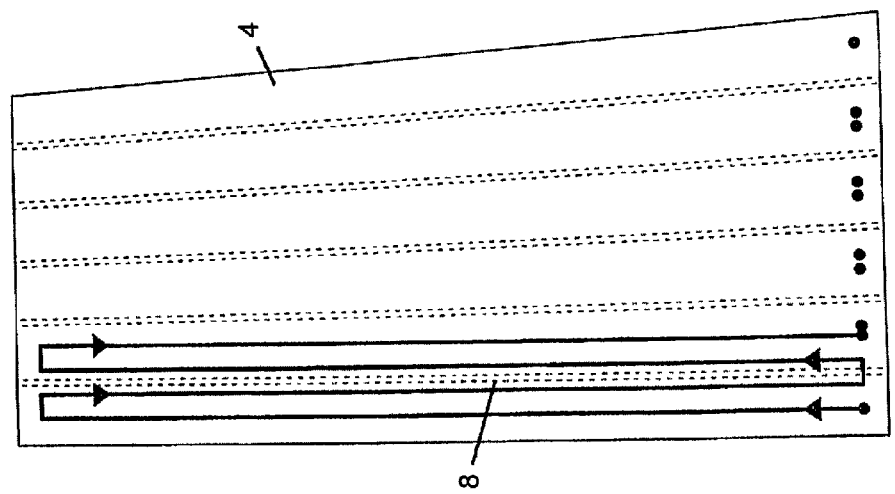
FIG. 11 is a diagram showing a top view of a wing box skin with a potential scan path plan (assuming installation of a runoff component at the wide end of the wing box) depicted as a serpentine line superimposed on the skin, which serpentine line represents a path of travel of a point on an NDI sensor during scanning of the skin using the apparatus depicted on the left-hand side of FIG. 10.

The usage setup for the configuration shown in FIG. 10 would be to position the tractor 12 and a portion of the NDI scanner trailer 68 on a run-on/run-off component (not shown in FIG. 10) attached to one end of the horizontal stabilizer, and start the scanning process by first moving the NDI sensor array to the starting position (e.g., the left side in this example), and then moving the tractor onto the wing box and then along the length of the wing box until the NDI sensor array reaches the other end of the wing box. After the tractor has been stopped, the NDI sensor array 40 is moved in the Y direction along the length of the central frame part 72 to its next index position (to the right in this example). After the array has been stopped, the tractor is moved in the opposite direction along the length of the wing box until the trailer is again situated on the run-on/run-off component. After the tractor has been stopped on the run-on/run-off component, the NDI sensor array is moved in the Y direction to its next index position. Again the array is stopped and the foregoing steps are repeated until the scan with the NDI sensor array in its final index position (the right-most position in this example) is completed. All of the components are then removed from spar 8a and moved to the next spar to be scanned, and the process is repeated. The path trace for this scanning mode when the apparatus is traveling along internal spar 8a is shown in FIG. 11. Path traces similar to the one shown in FIG. 11 will be generated for each internal spar of the wing box when the entire top skin 4 is scanned.

Figure 12:
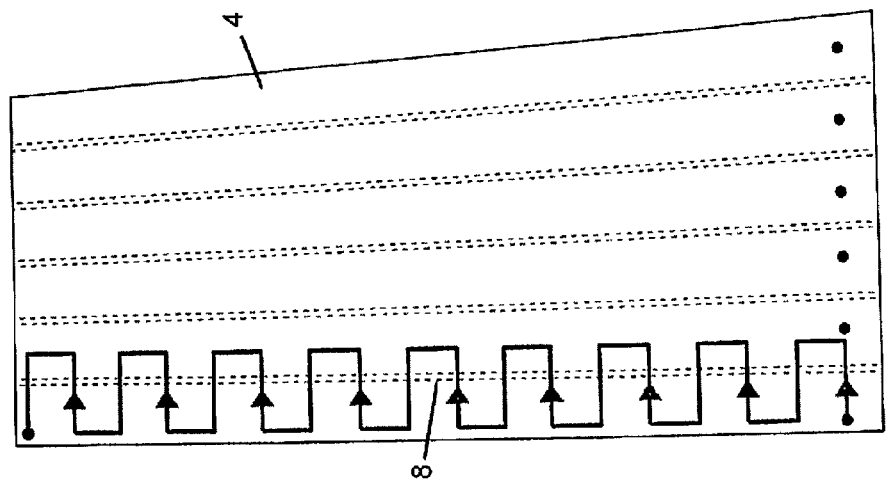
FIG. 12 is a diagram showing a top view of a wing box skin with a potential scan path plan (assuming installation of a runoff component at the wide end of the wing box) depicted as a serpentine line superimposed on the skin, which serpentine line represents a path of travel of a point on an NDI sensor during scanning of the skin using an apparatus that differs from that depicted on the left-hand side of FIG. 10 in that the scan plane of the NDI sensor unit is oriented parallel to the direction of tractor travel instead of perpendicular thereto.

In accordance with an alternative embodiment having a single tractor configuration, the scan plane of the NDI sensor array can be oriented perpendicular to the lead screw. The path trace for this scanning mode when the apparatus is traveling along internal spar 8a is shown in FIG. 12.

Using a single tractor would have several advantages over the double-tractor setup, but would require that the system scan a respective section of the horizontal stabilizer skin (approximately 2 feet wide) above each spar, and then move the tractor-trailer setup over to the next spar and repeat the process. For the horizontal stabilizer application described here, the single-tractor configuration would result in five sets of long NDI scan strips instead of one large scan. Accordingly, if something goes wrong with the large scan produced by the double-tractor configuration, the system operator may need to run the entire process again, but with the single-tractor configuration, the system operator would only need to re-run one of the five scan plans.

Figure 13:
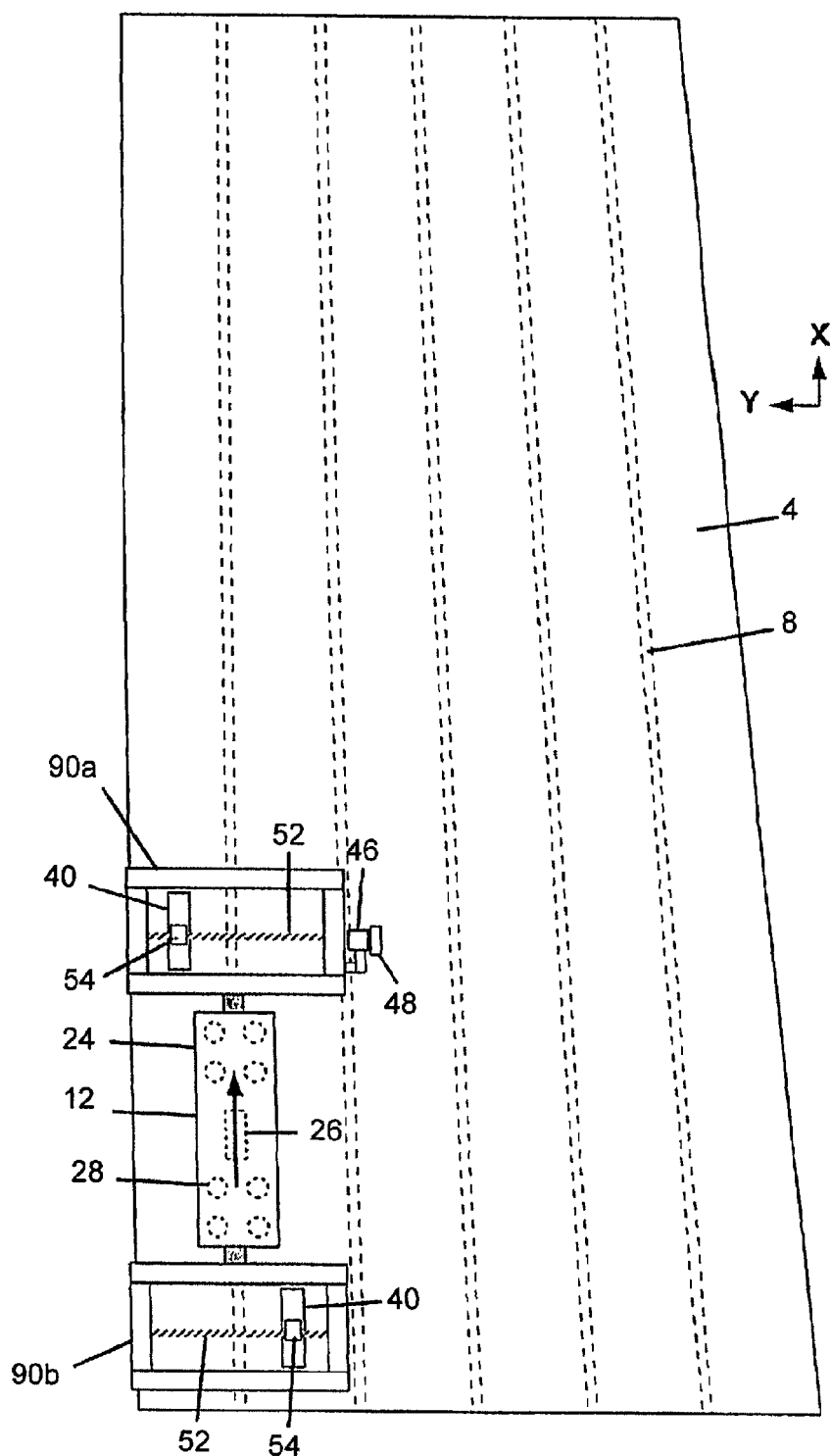
FIG. 13 is a diagram showing a top view of an external skin scanning apparatus atop a surface skin of a wing box, the apparatus comprising a single tractor coupled to front and rear NDI scanner trailers in accordance with a further embodiment. In this embodiment, the scan planes of the NDI sensor units are oriented parallel to and movable (relative to the tractor) in a direction perpendicular to the direction of tractor travel.

FIG. 13 shows a top view of an external skin scanning apparatus in accordance with a further embodiment. This apparatus has front and rear payload platforms 90a and 90b coupled to front and read ends of a tractor vehicle 12. In the scenario depicted in FIG. 13, the tractor vehicle 12 is traveling in the direction indicated by the arrow, in which case the tractor is pushing payload platform 90a and pulling payload platform 90b. Each payload platform 44a, 44b shown in FIG. 13 has a construction similar to that of payload platform 44 previously described with reference to FIG. 4, but is shorter in length.

The apparatus shown in FIG. 13 is equipped with front and rear NDI sensor units 40 which can be operated independently. When payload platform 90b overlies the lateral marginal strip of skin surface adjacent the root end of the wing box, its NDI sensor unit 40 can inspect that strip without using a run-on/run-off component. Likewise when payload platform 90a overlies the lateral marginal strip of skin surface adjacent the tip end of the wing box, its NDI sensor unit 40 can inspect that strip without using a run-on/run-off component.

An extension of the single tractor/single NDI scanner trailer setup shown in FIG. 10 is to have respective NDI scanner trailers connected to the front and rear of the tractor. This would allow faster scanning, and the NDI sensor array could reach the edges of both the root and tip ends of the horizontal stabilizer without changing the vehicle configuration. This option is shown in FIGS. 14, 14A and 14B.

Figure 14:
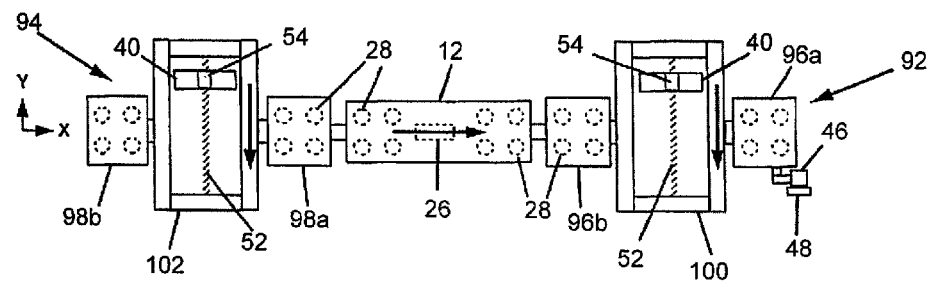
FIG. 14 is a diagram showing a top view of an external skin scanning apparatus comprising a single tractor coupled to front and rear NDI scanner trailers in accordance with a further embodiment. In this embodiment, the NDI sensor units are oriented perpendicular to and movable (relative to the tractor) in a direction perpendicular to the direction of tractor travel.
Figure 14A:
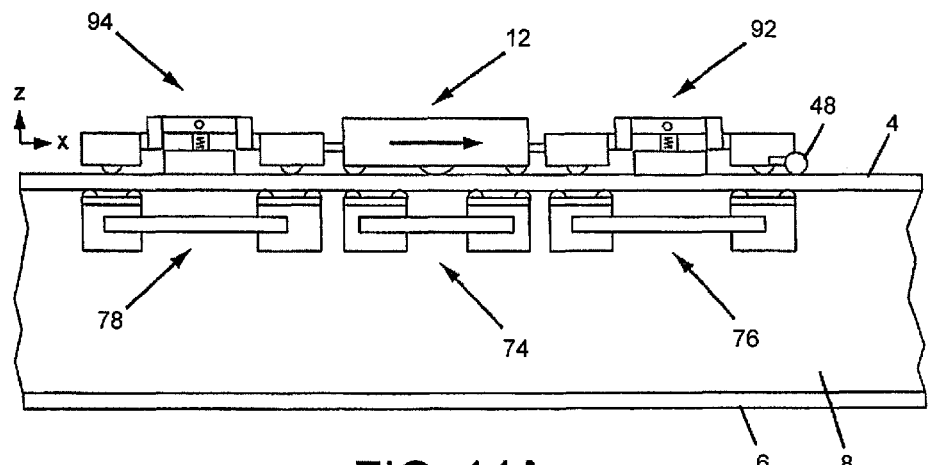
FIGS. 14A and 14B are diagrams showing a side view and an end view respectively of a configuration in which a scanning apparatus of the type shown in FIG. 14 is magnetically coupled to respective sets of passive trailer vehicles disposed on opposing sides of a spar and magnetically coupled to each other.
Figure 14B:
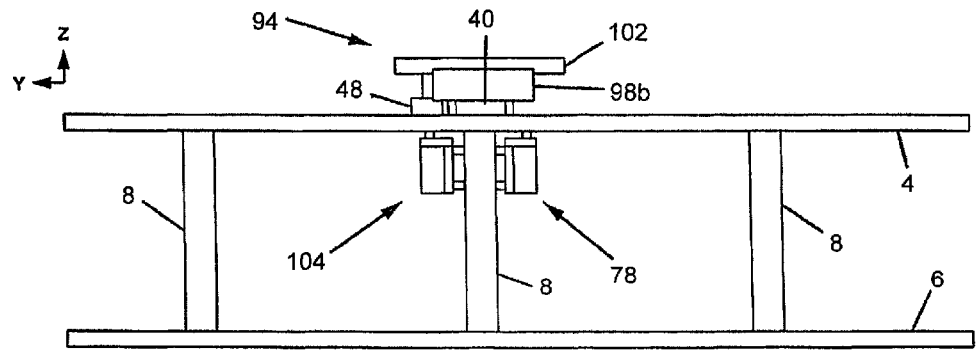

FIG. 14 shows a top view of an external skin scanning apparatus comprising a single tractor 12 coupled to front and rear NDI scanner trailers 92, 94 in accordance with a further embodiment. Each NDI scanner trailer vehicle comprises an NDI sensor array 40 slidably coupled to a respective frame. The frame of NDI scanner trailer 92 comprises first and second rolling frame parts 96a, 96b rigidly connected by a central frame part 100; the frame of NDI scanner trailer 94 comprises first and second rolling frame parts 98a, 98b rigidly connected by a central frame part 102. The coupled frames of tractor vehicle 12 and trailer vehicles 92, 94 form respective parts of a chassis, the three coupled chassis parts forming a mobile platform (consistent with terminology used in the appended claims). A rotation encoder 46 may be mounted to the frame of either NDI scanner trailer vehicle. In the implementation shown in FIG. 14, the rotation encoder 46 is mounted to the first rolling frame part 96a. An encoder wheel 48 is coupled to a rotation encoder 46 which outputs pulses for tracking the X positions of both NDI sensor arrays 40 (which are separated by a known distance). Optionally, a second rotation encoder/encoder wheel assembly could also be mounted to trailer vehicle 94. In addition, respective lead screw encoders (not shown in FIG. 14) can provide pulses indicating the Y positions of the NDI sensor arrays 40.

Each NDI sensor array 40 seen in FIG. 14 is slidably coupled to a respective central frame part 100, 102 having alignment guide elements (as previously described) that guide the NDI sensor array 40 along a linear path. Each NDI sensor array 40 is coupled to a respective drive nut 54. In the example depicted in FIG. 14, the scan planes of the NDI sensor arrays 40 are oriented perpendicular to the axis of lead screw 52. Alternatively, the scan planes could be parallel to the lead screw. Each NDI scanner trailer vehicle 92, 94 further comprises a motor (not shown) which drives rotation of the lead screw 52 and motors (not shown) for raising or lowering the magnets 28 which couple the NDI scanner trailer vehicles to internal passive trailer vehicles. In accordance with one implementation, the motor which drives rotation of the lead screw 52 can be mounted to the central frame part, while two motors for changing the elevation of respective groups of magnets (four magnets in each group) are respectively mounted to the first and second rolling frame parts.

In this embodiment, the scan plane of each NDI sensor unit 40 is oriented perpendicular to the lead screw 52 to which it is rotatably coupled (by means of a respective drive nut 54). Each NDI sensor unit 40 is movable in a direction perpendicular to the direction of tractor travel (indicated by an arrow in FIG. 14).

FIG. 14A shows a side view of a configuration in which a scanning apparatus of the type shown in FIG. 14 is magnetically coupled to respective sets of passive trailer vehicles disposed on opposing sides of a spar 8 and magnetically coupled to each other. FIG. 14A shows an inspection scenario wherein the scanning apparatus is atop the top skin 4. As shown in FIG. 14A, the tractor vehicle 12 and NDI scanner trailer vehicles 92, 94 can ride on the exterior surface of top skin 4. The tractor vehicle 12 and NDI scanner trailer vehicles 92, 94 are magnetically coupled to respective pairs of internal passive trailer vehicles. Each pair of internal passive trailer vehicles ride on the interior surface of the intervening skin and on opposing sides of spar 8. Three internal passive trailer vehicles 74, 76 and 78 are visible in FIG. 14A, within another set of three internal passive trailer vehicles being disposed behind spar 8. Thus the mobile platform shown in FIG. 14A includes nine vehicles which move in unison. The tractor vehicle 12 is coupled to NDI scanner trailer vehicles 92, 94, a first pair of internal passive trailer vehicles is coupled to tractor vehicle 12 and each other, a second pair of internal passive trailer vehicles is coupled to NDI scanner trailer vehicle 92 and each other, and a third pair of internal passive trailer vehicles is coupled to NDI scanner trailer vehicle 94 and each other.

FIG. 14B shows an end view of the apparatus depicted in FIG. 14A. Internal passive trailer vehicle 78, which is magnetically coupled to NDI scanner trailer vehicle 94 through skin 4, is also magnetically coupled to internal passive trailer vehicle 104 through spar 8, which is also magnetically coupled to NDI scanner trailer vehicle 94 through skin 4. The other internal passive trailer vehicles are not visible in the end view of FIG. 14B.

In this single-tractor design, a linear translational element (e.g., a lead screw) is used for moving the NDI sensor array laterally. However, there are other mechanisms that could be used for lateral positioning. For example, a linkage device or a multiple degree-of-freedom articulated arm can be used. These types of designs would lower the overall width of the system, which could be useful in passing through the horizontal stabilizer support tool, which will be discussed next.

Part Holding Tools

One feature of the skin scanning apparatus disclosed herein is its ability to run on the bottom as well as the top of the part being inspected. To run on the bottom, the externally mounted platform, i.e., the tractor vehicle and tool-carrying chassis parts, needs a clear path that avoids any structural supports. As part of this scanning system, part holding tools were designed that support the part at opposite ends thereof.

FIG. 15A shows side view of configurable tools that can be used to support a wing box 2 during non-destructive inspection using systems disclosed herein. One part holding tool (hereinafter "inboard support tool") 120 is designed to hold/support a wing box 2 near its root end; another part holding tool (hereinafter "outboard support tool") 126 is designed to hold/support wing box 2 near its tip end. These inboard and outboard part holding tools may be constructed differently to reflect the different sizes, shapes and weights of the root and tip ends of the wing box 2. As seen in FIG. 15A, a third part holding tool (hereinafter "alternate inboard support tool") 122 is designed to hold/support wing box 2 at an intermediate position closer to the position of inboard support tool 120 than to the position of outboard support tool 126, while a fourth part holding tool (hereinafter "alternate outboard support tool") 124 is designed to hold/support wing box 2 at an intermediate position closer to the position of outboard support tool 126 than to the position of inboard support tool 120.

Each support tool 120, 122, 124 and 126 comprises a respective pedestal 128 that stands on the ground and a frame 130 supported by the pedestal 128. Each support tool has movable support structure, i.e., a row of headers 132, arranged in a chordwise direction beneath the wing, which row of headers can be raised to provide support for the wing box 2 or lowered to provide a clear channel for passage of the externally mounted mobile platform during inspection of the bottom skin 6 of the wing box 2. Each row of headers is attached to and vertically displaceable by pistons of a respective pair of pneumatic cylinders (not shown) situated on opposite sides of a respective frame 130. Each row of headers can be moved up and down independently. Each pneumatic cylinder can be selectively supplied with pressurized air from a source via an air distribution system (not shown). In one implementation, the pneumatic cylinders are actuated by manual operation of header controls. In other embodiments, the air flow to the pneumatic cylinders can be automated and be included as an instruction in the motion path plan.

In order for the skin scanning apparatus shown in FIG. 4 to be able to scan the full range of both the top and bottom aerodynamic surfaces, the wing box support system shown in FIG. 15A can be configured to allow the external mobile platform (which carries one or more NDI sensor arrays) to get past the headers of the support tools.

For some single-tractor configurations, it may be sufficient to simply provide pass-through openings of sufficient width between the extended headers of inboard and outboard support tools 120 and 126 while the headers of alternate inboard and outboard support tools 122 and 124 remain in a retracted state. But for double-tractor configurations (such as the apparatus shown in FIG. 4), all of the headers of any one of the support tools would need to be retracted in order to allow the externally mounted mobile platform to pass between that support tool and the bottom skin 6 of the wing box 2.

FIGS. 15A through 15C show three configurations which may occur during a configuration change sequence that enables the bottom skin 6 to be inspected along its entire length while maintaining vertical support of the wing box 2. In the first stage of the configuration change process (shown in FIG. 15A), an externally mounted NDI scanner platform 140 starts to the left of the inboard support tool 120 while the headers 132 of inboard and outboard support tools 120 and 126 are in their extended positions to support the wing box 2 and the headers 132 of alternate inboard and outboard support tools 122 and 124 are retracted.

In the second stage (shown in FIG. 15B), the headers of the alternate inboard support tool 122 are extended (i.e., raised) to support the wing box 2 and the headers of the inboard support tool 120 are retracted (i.e., lowered) so that the wing box is now supported by alternate inboard support tool 122 and outboard support tool 126. In this configuration, the NDI scanner platform 140 can be moved through the space previously obstructed by the extended headers 132 of inboard support tool 120 to a position whereat the NDI scanner array overlies a space located between the inboard support tool 120 and the alternate inboard support tool 122.

In the third stage (shown in FIG. 15C), the headers of the inboard support tool 120 are extended to support the wing box 2 and the headers of the alternate inboard support tool 122 are retracted so that the wing box is now again supported by the inboard and outboard support tools 120 and 126. In this configuration, the NDI scanner platform 140 can be moved through the space previously obstructed by the extended headers of alternate inboard support tool 122 to a position whereat the NDI scanner array overlies a space located between the alternated inboard and outboard support tools 122 and 124.

A similar process happens when the mobile platform 140 reaches the outboard support tooling. Note that the vertical support transition only needs to take place when the wide section of the mobile platform passes through the support region, since the tractor vehicle already fits in and can be passed through the space between adjacent headers in the support tool.

Other System Use Cases

Up to this point, only initial inspection during manufacturing has been discussed, in which case the number of obstructions on the surfaces is minimized (since other components have not been attached yet), but use of this system for in-service inspection is also a possibility. One problem with in-service inspection would be avoiding fasteners through the flanges of the wing box. This is mainly a concern for the magnetically coupled followers. Some interfering parts on the object being scanned may be removed during inspection, but for those that cannot be removed, one option here is to modify the shape of the magnetically coupled followers to have gaps or cutouts to allow the to fasteners to pass under the followers.

One existing solution for wing box inspection uses a gantry system to position the NDI sensor array. That system is large and expensive, is installed in a fixed position, and takes additional training to operate. The apparatus disclosed herein is less expensive, smaller, portable, and is compatible with the system disclosed in U.S. patent application Ser. No. 13/534, 014, which would require less additional training for operators. The gantry-based solution requires that the horizontal stabilizer be turned over in order to scan the other aerodynamic surface. This step would not be needed using the process disclosed herein.

Computer System and Software

Regardless of which configuration is used, the active system components can be controlled by a computer system in response to commands input via a graphical user interface by the system operator or through an automated process using pre-planned motion instructions to control the system. The motors onboard the trailer vehicles and NDI scanner trailer vehicles or platforms are connected to an electronic control box by means of flexible electrical cables. The electronic control box contains the system power supplies and integrates all the scanner control connections and provides an interface between the computer and the scanners and tractor.

Figure 16:
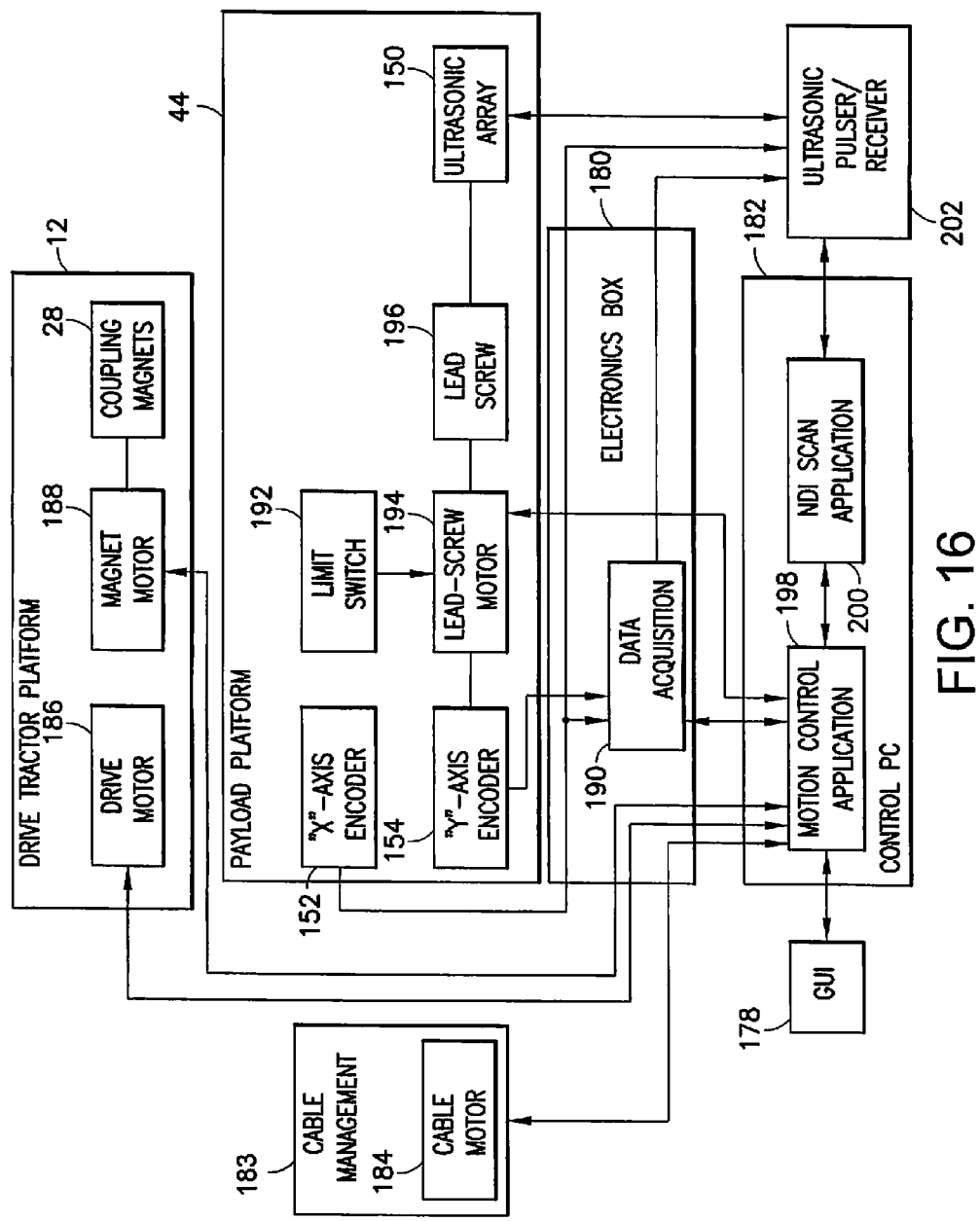
FIG. 16 is a block diagram showing a control system in accordance with one embodiment.

FIG. 16 is a block diagram showing some components of a control system in accordance with the embodiment depicted in FIG. 10. The control system comprises a ground-based computer 182 programmed with motion control application software 198 and NDI scan application software 200. The two-way communication between these software modules (indicated by a two-headed arrow in FIG. 16) is optional. In the alternative, the motion control application software 198 and NDI scan application software 200 could be run on separate computers.

In the embodiment shown in FIG. 16, the control computer 182 is connected to a drive tractor platform in the form of a tractor vehicle 12 and to a payload platform 44 by flexible electrical cables that connect to an electronics relay/switch box 180. The electronic relay/switch box 180 contains the system power supplies, relays, and a data acquisition device 190, and integrates all the scanner control connections and provides an interface between the computer 182 and the tractor vehicle 12, the payload platform 44, and a cable management system 183

The computer 182 may comprise a general-purpose computer programmed with motion control application software 198 comprising respective software modules for controlling drive motor 186 and magnet vertical positioning motors 188 onboard the drive tractor platform 12, lead-screw motor 194 onboard the payload platform 44, and cable motor 184 of the cable management system 183. Each magnet motor 188 displaces a group of tractor coupling magnets 28 as disclosed in U.S. patent application Ser. No. 13/313,267. Motion control application software 198 controls the lead screw motor 194 to drive rotation of the lead screw 196, which rotation causes the ultrasonic transducer array 150 to scan in a Y direction. The lead screw 196 is connected to an output shaft of the lead screw motor 194. The range of motion of the ultrasonic transducer array 150 in both Y directions is limited by limit switches 192. A Y-axis encoder 154 measures the angular position of the output shaft of lead screw motor 194, which angular position is proportional to the Y position of the ultrasonic transducer array 150. The motion control application software 198 is capable of moving array 150 in the Y direction and tractor 12 in the X direction independently and alternatingly. The X and Y positions of the ultrasonic transducer array 150 are respectively measured by pulses output from the X- and Y-axis encoders 152, 154.

In accordance with one embodiment, the encoded data from both encoders 152 and 154 is received by a data acquisition device 190 via a relay switch and a splitter (not shown) inside the electronics box 180. The data acquisition device 190 also has digital input and output connections that are used for multiple functions within the system. In accordance with other embodiments in which alternate forms of the NDI sensor actuator mechanism (such as a linkage-based mechanism) do not produce linear output motion, the data acquisition device 190 may be used to generate quadrature pulses that simulate the encoder pulses which would be outputted if a position encoder were arranged to output pulses representing the Y position of ultrasonic transducer array 150. These simulated encoder pulses are sent to the ultrasonic pulser/receiver 202. The ultrasonic pulser/receiver also receives pulses generated by the X-axis encoder 152 via the aforementioned switch and splitter (not shown in FIG. 16) inside the electronic box 180. The pulser/receiver 202 sends the encoder pulses to the NDI scan software 200. The NDI scanning software application 200 interprets the simulated encoder pulses as Y-encoder values, which are used (along with the X-encoder values) to position the scan data from array 150 in the proper locations.

The computer 182 may also host NDI scan acquisition and display software 200 that controls the ultrasonic pulser/receiver 202. The ultrasonic pulser/receiver 202 in turn sends pulses to and receives return signals from the ultrasonic transducer array 150. The NDI scan application software 200 controls all details of the scan data and the display of data. In the embodiment shown in FIG. 16 the pulser/receiver 202 correlates the acquired ultrasonic data with the encoder data received from the data acquisition device 190.

The motion control application software 198 also controls a motor 184 of the cable management system 183. There are several cables that need to accompany the scanner and the tractor down the length of the box being inspected. The cable management system automatically feeds out the cables or pulls in the slack as the vehicles move. The cable management system 183 consists of two sets of motorized wheels (not shown) that grip the cables. The cable motor 184 is under computer control by way of control PC 182 and motion control software 198, which synchronizes the cables with the movement of the tractor, extending or retracting the cables as appropriate.

Software on the computer that controls the movement of the motors on the tractor, trailer, and cable management device allows scriptable motion plans to be created and executed to produce automated motion control of the system. Operators can load and activate custom motion path plans using a graphical use interface 178, which shows the status of the scanning process displayed on a virtual representation of the horizontal stabilizer. The graphical use interface 178 may be of the type disclosed in U.S. patent application Ser. No. 13/534,014. In addition to initiation of automated motion, the graphical user interface 178 also allows the operator to issue direct motion commands.

Figure 17:
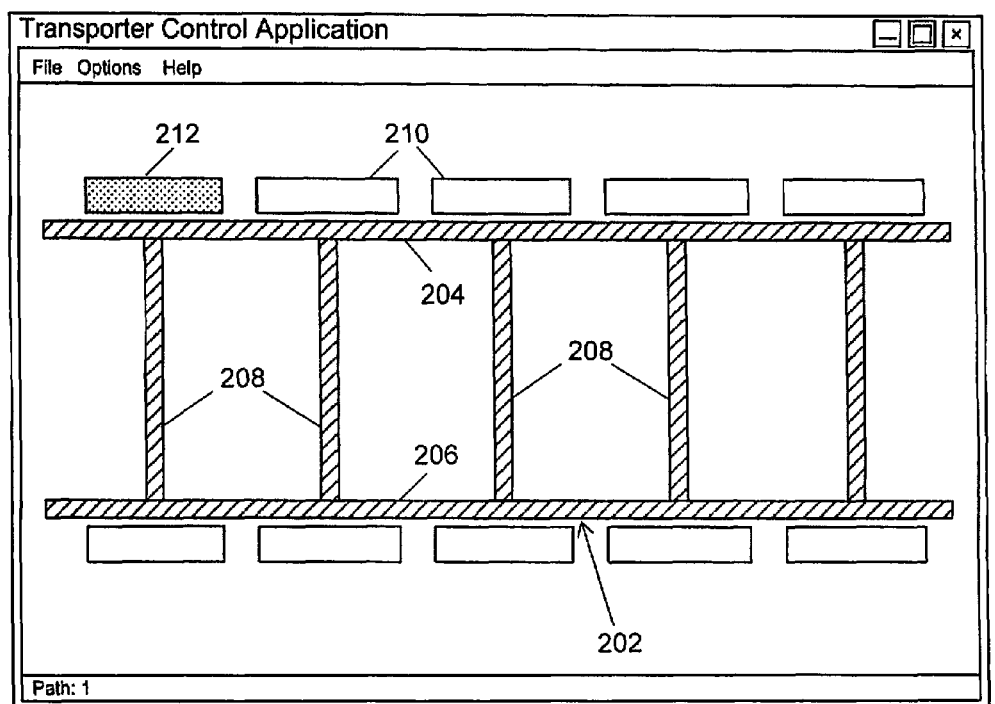
FIG. 17 is a diagram representing a screen shot of a graphical user interface for controlling the inspection system disclosed herein.

FIG. 17 is a diagram representing a screen shot 200 of a graphical user interface in accordance with one embodiment. Each graphical user interface display dialog (not shown) displays a two-dimensional visual representation 202 of the target object to be scanned, which in this example is a horizontal stabilizer. In this visual representation, the horizontal bands 204 and 206 respectively represent top and bottom skins of the horizontal stabilizer, while vertical bands 208 represent the spars which connect the top and bottom skins. Layered over the two-dimensional target object representation are a series of virtual buttons 210 (hereinafter "buttons") that represent the individual motion paths that can be selected and executed. Internally these buttons are associated with specific motion script files stored in the control PC that contain the parameters associated with that specific path. The buttons 210, which can be used to select the active motion path, are positioned in a way that they correspond to the actual position of the scanning devices on the part being scanned from the operator's point of view. This one-to-one correspondence makes it easier to keep track of which motion path sequence will be used, as well as marking which scans have been completed. The current motion path is indicated by a shaded button 212; empty buttons 210 indicate which scans have not been completed yet. This symbology helps the operator keep track of the current scan path, the areas that have been scanned, and the areas that still need to be scanned. This graphical user interface gives a simple visual representation that is easy to use and can be operated with little additional training.

In accordance with the embodiments described above, a control computer is provided with encoder information concerning the spanwise and chordwise positions of the inspection chassis relative to the frame of reference of the wing box being inspected. In the alternative, this functionality can be provided by any one of a multiplicity of known positional tracking mechanisms. In accordance with various alternative embodiments, an optical tracking system can be used to determine the spanwise position of the inspection. For example, U.S. Pat. No. 7,643,893 discloses a motion capture system wherein multiple motion capture cameras are set up around the object to be scanned to create a three-dimensional capture volume that captures motion for all six degrees-of-freedom of the object being tracked. Alternatively, the optical tracking mechanism may comprise a local positioning system of the type disclosed in U.S. Pat. No. 7,859,655.

In addition to NDI-specific types of inspection, other types of inspection or manufacturing applications may be able to take advantage of the mechanical and control concepts presented here. For example, the NDI sensor carried by the payload platform can be replaced by other components, such as: laser scanners, video cameras, robotic manipulators, reflective targets, paint heads, or other electro-mechanical components.

While skin scanning systems have been described with reference to various embodiments, it will be understood by those skilled in the art that various changes may be made and equivalents may be substituted for elements thereof without departing from the scope of the teachings herein. In addition, many modifications may be made to adapt the teachings herein to a particular situation without departing from the scope thereof. Therefore it is intended that the claims not be limited to the particular embodiments disclosed herein.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices comprising a processing unit (e.g., a central processing unit) and some form of memory (i.e., computer-readable medium) for storing a program which is readable by the processing unit.

The method claims set forth hereinafter should not be construed to require that the steps recited therein be performed in alphabetical order (alphabetical ordering in the claims is used solely for the purpose of referencing previously recited steps) or in the order in which they are recited. Nor should they be construed to exclude any portions of two or more steps being performed concurrently or alternatingly.

The invention claimed is:

1. A method for scanning a wing box skin, comprising:
    (a) placing a first tractor vehicle in a position external to the wing box and in contact with the skin;
    (b) placing first and second trailer vehicles in respective interior spaces of the wing box with a first spar of the wing box therebetween;
    (c) magnetically coupling the first and second trailer vehicles to the first tractor vehicle with the skin therebetween and to each other with the first spar therebetween;
    (d) coupling a payload platform to the first tractor vehicle in a position external to the wing box, the payload platform comprising a frame and a maintenance tool that is movable relative to the frame;
    (e) moving the first tractor vehicle along a path that follows the first spar;
    (f) stopping the first tractor vehicle; and
    (g) moving the maintenance tool of the payload platform in a first direction relative to the frame of the payload platform while the first tractor vehicle is stopped in step (f).

2. The method as recited in claim 1, wherein during step (g) the maintenance tool of the payload platform moves laterally relative to the first spar.

3. The method as recited in claim 1, further comprising:
    (h) placing a second tractor vehicle in a position external to the wing box and in contact with the skin;
    (i) placing third and fourth trailer vehicles in respective interior spaces of the wing box with a second spar of the wing box therebetween;
    (j) magnetically coupling the third and fourth trailer vehicles to the second tractor vehicle with the skin therebetween and to each other with the second spar therebetween;
    (k) coupling the payload platform to the second tractor vehicle;
    (l) during step (e), moving the second tractor vehicle along a path that follows the second spar; and
    (m) stopping the second tractor vehicle,
    wherein step (g) is performed while the first and second tractor vehicles are not moving.

4. The method as recited in claim 3, wherein the first and second spars are not parallel.

5. The method as recited in claim 1, further comprising:
    (h) stopping the maintenance tool;
    (i) moving the first tractor vehicle further along the path that follows the first spar;
    (j) stopping the first tractor vehicle; and
    (k) after step (j), moving the maintenance tool of the first payload platform in a second direction relative to the frame of the payload platform while the first tractor vehicle is stopped in step (j), said second direction being opposite to said first direction.

6. The method as recited in claim 1, further comprising actuating the maintenance tool to transmit beams toward the skin.

7. The method as recited in claim 1, wherein the maintenance tool comprises an array of transducer elements configured to scan in a scan plane, said scan plane being oriented parallel to the first spar.

8. The method as recited in claim 1, wherein the maintenance tool comprises an array of transducer elements configured to scan in a scan plane, said scan plane being oriented perpendicular to the first spar.

9. The method as recited in claim 1, further comprising:
    placing first, second and third wing box support tools under the wing box, said first wing box support tool being closer to a root end of the wing box than is the second wing box support tool and the third wing box support tool being closer to a tip end of the wing box than is the second wing box support tool, each of the first, second and third wing box support tools being configurable between a first state wherein it supports the wing box and obstructs the payload platform and a second state wherein it neither supports the wing box nor obstructs the payload platform;

configuring the first, second and third wing box support tools so that the second and third wing box support tools support the wing box while the first wing box support tools does not;

while the second and third wing box support tools are supporting the wing box, moving the first tractor vehicle from a position whereat the payload platform overlies a space between the root end of the wing box and the first wing box support tool to a position whereat the payload platform overlies a space between the first and second wing box support tools;

after the preceding step has been performed, reconfiguring the first and second wing box support tools so that the first and third wing box support tools support the wing box while the second wing box support tools does not; and while the first and third wing box support tools are supporting the wing box, moving the first tractor vehicle from the position whereat the payload platform overlies a space between the first and second wing box support tools to a position whereat the payload platform overlies a space between the second and third wing box support tools.

10. An apparatus for scanning a wing box skin, comprising:

a first tractor vehicle comprising a first frame, a plurality of wheels rotatably coupled to said first frame, a first coupling element, a first plurality of magnets supported by said first frame, a first drive wheel for driving said first tractor vehicle to move, and a first motor for driving rotation of said first drive wheel, said first motor being supported by said first frame; and a first payload platform comprising a second frame, a plurality of wheels rotatably coupled to said second frame, a second coupling element, a first maintenance tool supported by and movable relative to said second frame, and a first actuator for moving said first maintenance tool relative to said second frame, said first actuator being supported by said second frame, wherein first and second coupling elements are coupled to each other.

11. The apparatus as recited in claim 10, wherein said actuator comprises a lead screw and a motor for driving rotation of said lead screw.

12. The apparatus as recited in claim 10, wherein said first payload platform further comprises a second plurality of magnets supported by said second frame.

13. The apparatus as recited in claim 10, further comprising a second tractor vehicle, said second tractor vehicle comprising a third frame, a plurality of wheels rotatably coupled to said third frame, a third coupling element, a second plurality of magnets supported by said third frame, a second drive wheel for driving said second tractor vehicle to move, and a second motor for driving rotation of said second drive wheel, said second motor being supported by said second frame, wherein said first payload platform further comprises a fourth coupling element, said third and fourth coupling elements being coupled to each other.

14. The apparatus as recited in claim 13, wherein said first coupling element is pivotable relative to said second coupling element, and said third coupling element is pivotable and slidable relative to said fourth coupling element.

15. The apparatus as recited in claim 13, wherein said first and second coupling elements form a rotating joint, and said third and fourth coupling elements form a sliding and rotating joint.

16. The apparatus as recited in claim 10, further comprising a second payload platform comprising a third frame, a plurality of wheels rotatably coupled to said third frame, a third coupling element, a second maintenance tool supported by and movable relative to said third frame, and a second actuator for moving said second maintenance tool relative to said third frame, said second actuator being supported by said third frame, wherein said first tractor vehicle further comprises a fourth coupling element, said third and fourth coupling elements being coupled to each other.

17. The apparatus as recited in claim 10, wherein said first maintenance tool comprises a linear array of transducer elements.

18. A system comprising the apparatus as recited in claim 10 and a hollow composite structure, said hollow structure comprising a spar and first and second skins connected by said spar, and said apparatus being in contact with an external surface of said first skin and overlying a portion of said spar, said system further comprising:

a first trailer vehicle disposed under said first skin and adjacent to one side of said spar, said first trailer vehicle comprising a third frame, a plurality of wheels rotatably coupled to said third frame and in contact with an internal surface of said first skin, and a second plurality of magnets supported by said third frame, at least one magnet pole of said second plurality of magnets being magnetically coupled through said first skin to a respective magnet pole of said first plurality of magnets; and a second trailer vehicle disposed under said first skin and adjacent to another side of said spar, said second trailer vehicle comprising a fourth frame, a plurality of wheels rotatably coupled to said fourth frame and in contact with an internal surface of said first skin, and a third plurality of magnets supported by said fourth frame, at least one magnet pole of said third plurality of magnets being magnetically coupled through said first skin to a respective magnet pole of said first plurality of magnets, wherein at least one magnet pole of said second plurality of magnets is magnetically coupled through said spar to a respective magnet pole of said third plurality of magnets.

19. A system for performing a maintenance function on a wing box skin, comprising:

(a) a hollow composite structure comprising first and second spars and first and second skins connected by said first and second spars;

(b) a mobile platform comprising:

(i) a chassis comprising first and second chassis parts coupled to each other, said first chassis part overlying a first portion of said first spar, each of said first and second chassis parts comprising a respective plurality of wheels in contact with said external surface of said first skin;

(ii) a first drive wheel rotatably coupled to said first chassis part and in contact with said external surface of said first skin;

(iii) a first actuator mounted to said first chassis part for causing said first drive wheel to rotate;

(iv) a first plurality of magnets mounted to said first chassis part; and (v) a first maintenance tool slidably coupled to said second chassis part, said first maintenance tool being slidable along said second chassis part; and (vi) a second actuator mounted to said second chassis part for causing said first maintenance tool to slide along said second chassis part;

(c) a first trailer vehicle disposed adjacent a first portion of an internal surface of said first skin and adjacent one side of said first spar, said first trailer vehicle comprising a second plurality of magnets, at least one magnet pole of said second plurality of magnets being magnetically coupled to a magnet pole of said first plurality of magnets through said first skin; and (d) a second trailer vehicle disposed adjacent a second portion of an internal surface of said first skin and adjacent another side of said first spar, said second trailer vehicle comprising a third plurality of magnets, at least one magnet pole of said third plurality of magnets being magnetically coupled to a magnet pole of said first plurality of magnets through said first skin, and at least one magnet pole of said third plurality of magnets being magnetically coupled to a magnet pole of said second plurality of magnets through said first spar, wherein said magnetically coupled mobile platform and first and second trailer vehicles move in unison when said drive wheel is rotated.

20. The system as recited in claim 19, wherein said first maintenance tool is an inspection unit, said mobile platform further comprises means for measuring an X position and a Y position of said inspection unit, and said system further comprises a pulser/receiver unit operatively coupled to said inspection unit and to said first and second encoding means, said pulser/receiver unit being programmed to perform the following operations:

sending control signals to said inspection unit;
receiving scan data signals from said inspection unit;
receiving X-Y position data signals from said measuring means; and
correlating said scan data with said X-Y position data.

21. The system as recited in claim 19, further comprising:
a plurality of motion script files containing sequences of motion commands and parameters respectively associated with a plurality of motion paths; and
a computer system programmed to execute a sequence of commands in a selected one of plurality of motion scripts, said sequence of commands controlling operation of said first and second actuators to cause said first maintenance tool to move along a corresponding selected one of said motion paths in accordance with its associated parameters.

22. The system as recited in claim 19, wherein said chassis further comprises a third chassis part coupled to said second chassis part, said third chassis part comprising a respective plurality of wheels in contact with said external surface of said first skin, said third chassis part overlying a portion of said second spar, wherein said mobile platform further comprises:

(vi) a second drive wheel rotatably coupled to said third chassis part and in contact with said external surface of said first skin, said third chassis part being movable along a third motion path when said second drive wheel rotates while in contact with said external surface of said first skin;
(vii) a second actuator mounted to said third chassis part for causing said second drive wheel to rotate;
(viii) a fourth plurality of magnets mounted to said third chassis part;
(ix) a third encoder for measuring a position of said third chassis part along said third motion path, and
wherein said system further comprises:
(e) a third trailer vehicle disposed adjacent a third portion of an internal surface of said first skin and adjacent one side of said second spar, said third trailer vehicle comprising a fifth plurality of magnets, at least one magnet pole of said fifth plurality of magnets being magnetically coupled to a magnet pole of said fourth plurality of magnets through said first skin; and
(f) a fourth trailer vehicle disposed adjacent a fourth portion of an internal surface of said first skin and adjacent another side of said second spar, said second trailer vehicle comprising a sixth plurality of magnets, at least one magnet pole of said sixth plurality of magnets being magnetically coupled to a magnet pole of said fourth plurality of magnets through said first skin, and at least one magnet pole of said sixth plurality of magnets being magnetically coupled to a magnet pole of said fifth plurality of magnets through said second spar.

23. The system as recited in claim 19, wherein said first chassis part is pivotably coupled to said second chassis part, and said third chassis part is pivotably coupled and slidably coupled to said second chassis part.

24. The system as recited in claim 19, wherein said chassis further comprises a third chassis part coupled to said first chassis part, said third chassis part comprising a respective plurality of wheels in contact with said external surface of said first skin, said third chassis part overlying a second portion of said first spar, wherein said mobile platform further comprises:

(vi) a second maintenance tool slidably coupled to said third chassis part, said second maintenance tool being slidable along said third chassis part; and
(vii) a third actuator mounted to said third chassis part for causing said second maintenance tool to slide along said third chassis part.

* * * * *